US011826077B2

(12) United States Patent
Venturini et al.

(10) Patent No.: US 11,826,077 B2
(45) Date of Patent: Nov. 28, 2023

(54) EXTERNAL FIXATION STRUT

(71) Applicants: Orthofix S.R.L., Bussolengo (IT); TEXAS SCOTTISH RITE HOSPITAL FOR CHILDREN, Dallas, TX (US)

(72) Inventors: Daniele Venturini, Povegliano Veronese (IT); Andrea Ottoboni, Giacciano con Baruchella (IT); Gianluca Milano, Verona (IT); John D. Ross, Ovilla, TX (US); Karen D. Standefer, Flower Mound, TX (US); Mikhail L. Samchukov, Coppell, TX (US); Alexander M. Cherkashin, Flower Mound, TX (US)

(73) Assignees: Texas Scottish Rite Hospital for Children, Dallas, TX (US); Orthofix S.R.L., Verona (IT)

( * ) Notice: Subject to any disclaimer, the term of this patent is extended or adjusted under 35 U.S.C. 154(b) by 558 days.

(21) Appl. No.: 16/827,269

(22) Filed: Mar. 23, 2020

(65) Prior Publication Data
US 2021/0290270 A1 Sep. 23, 2021

(51) Int. Cl.
*A61B 17/64* (2006.01)
*A61B 17/62* (2006.01)

(52) U.S. Cl.
CPC .......... *A61B 17/6466* (2013.01); *A61B 17/62* (2013.01)

(58) Field of Classification Search
CPC ...................... A61B 17/62; A61B 17/64–6491
See application file for complete search history.

(56) References Cited

U.S. PATENT DOCUMENTS

| 4,294,254 | A |   | 10/1981 | Chamness |
| 4,308,863 | A | * | 1/1982 | Fischer ................. A61B 17/62 |
|           |   |   |        | 606/56 |

(Continued)

FOREIGN PATENT DOCUMENTS

| CN | 103494634 A | 1/2014 |
| EP | 2085037 | 7/2013 |

(Continued)

OTHER PUBLICATIONS

European Patent Office, European Search Report, Application No. EP 20 16 4789, dated Nov. 25, 2020, 4 pages, Munich.

(Continued)

*Primary Examiner* — Nicholas J Plionis
(74) *Attorney, Agent, or Firm* — Haynes and Boone, LLP

(57) ABSTRACT

An external fixation strut includes an elongated body including first and second tubular shafts. Opposite connectors are respectively coupled to one of the shafts and include a ball and socket joint. One shaft has an internal diameter slightly larger than the external diameter of the other to host the other shaft in a slidably and telescopic manner. The shafts of the strut are a synthetic radiolucent plastic material. A clamp element is in proximity of overlapping ends of the shafts for fast gripping action stopping the sliding of one shaft inside the other. A fixation element is manually operated and acts on the clamp element. A sleeve is provided around the central portion of the strut where the shafts overlap. The clamp element is a clamp band around the sleeve and includes opposite and facing gripping portions. The gripping portions are connected by a threaded connector of the fixation element.

26 Claims, 17 Drawing Sheets

(56) References Cited

U.S. PATENT DOCUMENTS

| | | |
|---|---|---|
| 5,180,380 A | 1/1993 | Pursley et al. |
| 5,314,426 A | 5/1994 | Pohl et al. |
| 5,429,638 A | 7/1995 | Muschler et al. |
| 5,451,225 A | 9/1995 | Ross, Jr. et al. |
| 5,626,579 A | 5/1997 | Muschler et al. |
| 5,628,740 A | 5/1997 | Mullane |
| 5,769,851 A | 6/1998 | Veith |
| 5,863,292 A | 1/1999 | Tosic |
| 5,871,484 A | 2/1999 | Spievack et al. |
| 5,928,230 A | 7/1999 | Tosic |
| 5,935,127 A | 8/1999 | Border |
| 6,024,745 A | 2/2000 | Faccioli et al. |
| 6,030,386 A | 2/2000 | Taylor et al. |
| 6,439,914 B2 | 8/2002 | Nimura et al. |
| 8,057,474 B2 | 11/2011 | Knuchel et al. |
| 8,162,984 B2 | 4/2012 | Weirich et al. |
| 8,172,885 B2 | 5/2012 | Songer et al. |
| 8,187,308 B2 | 5/2012 | Mullaney et al. |
| 8,197,490 B2 | 6/2012 | Pool et al. |
| 8,221,467 B2 | 7/2012 | Butler et al. |
| 8,388,619 B2 | 3/2013 | Mullaney |
| 8,419,732 B2 | 4/2013 | Mullaney |
| 8,444,644 B2 * | 5/2013 | Ross ................. A61B 17/6475 606/56 |
| 8,506,566 B2 | 8/2013 | Karidis et al. |
| 8,574,232 B1 * | 11/2013 | Ross ....................... A61F 5/042 606/57 |
| 8,679,117 B2 | 3/2014 | Knuchel et al. |
| 9,078,700 B2 | 7/2015 | Ross et al. |
| 9,872,706 B1 | 1/2018 | Mullaney et al. |
| 9,949,758 B2 | 4/2018 | Vikinsky et al. |
| 10,130,391 B2 | 11/2018 | Ross et al. |
| 10,932,820 B2 * | 3/2021 | Lauf ..................... A61B 17/62 |
| 2002/0165500 A1 | 11/2002 | Bechtold et al. |
| 2005/0143735 A1 | 6/2005 | Kyle |
| 2005/0192572 A1 | 9/2005 | Abdelgany et al. |
| 2005/0234457 A1 | 10/2005 | James et al. |
| 2006/0025769 A1 | 2/2006 | Dick et al. |
| 2006/0052782 A1 | 3/2006 | Morgan et al. |
| 2007/0049930 A1 | 3/2007 | Hearn et al. |
| 2007/0055234 A1 | 3/2007 | McGrath et al. |
| 2007/0118122 A1 | 5/2007 | Butler et al. |
| 2007/0118125 A1 | 5/2007 | Orbay et al. |
| 2007/0123858 A1 | 5/2007 | Strub et al. |
| 2007/0173837 A1 | 7/2007 | Chan et al. |
| 2009/0036892 A1 * | 2/2009 | Karidis ................. A61B 17/66 606/60 |
| 2010/0312243 A1 * | 12/2010 | Ross ....................... A61B 17/64 606/56 |
| 2011/0208187 A1 * | 8/2011 | Wong ................. A61B 17/6416 606/56 |
| 2012/0209269 A1 | 8/2012 | Pool et al. |
| 2012/0303028 A1 | 11/2012 | Wong et al. |
| 2013/0023876 A1 | 1/2013 | Rabiner et al. |
| 2014/0066931 A1 * | 3/2014 | Myers ................ A61B 17/6425 606/59 |
| 2014/0276817 A1 * | 9/2014 | Murray ................. A61B 17/62 606/56 |
| 2014/0276821 A1 | 9/2014 | Murray et al. |
| 2016/0199099 A1 * | 7/2016 | Myers ................ A61B 17/6458 606/59 |
| 2018/0228515 A1 * | 8/2018 | Ross .................. A61B 17/6491 |
| 2018/0368887 A1 * | 12/2018 | Lauf ....................... A61B 17/62 |
| 2019/0125407 A1 * | 5/2019 | Lauf .................. A61B 17/6425 |
| 2020/0000492 A1 | 1/2020 | Samchukov et al. |

FOREIGN PATENT DOCUMENTS

| | | |
|---|---|---|
| EP | 3245966 A1 | 11/2017 |
| WO | 2009018349 | 2/2009 |
| WO | 2009102904 | 8/2009 |

OTHER PUBLICATIONS

International Search Report and Written Opinion, PCT/US2015/026719, dated Jun. 30, 2015, 12 pages.

* cited by examiner

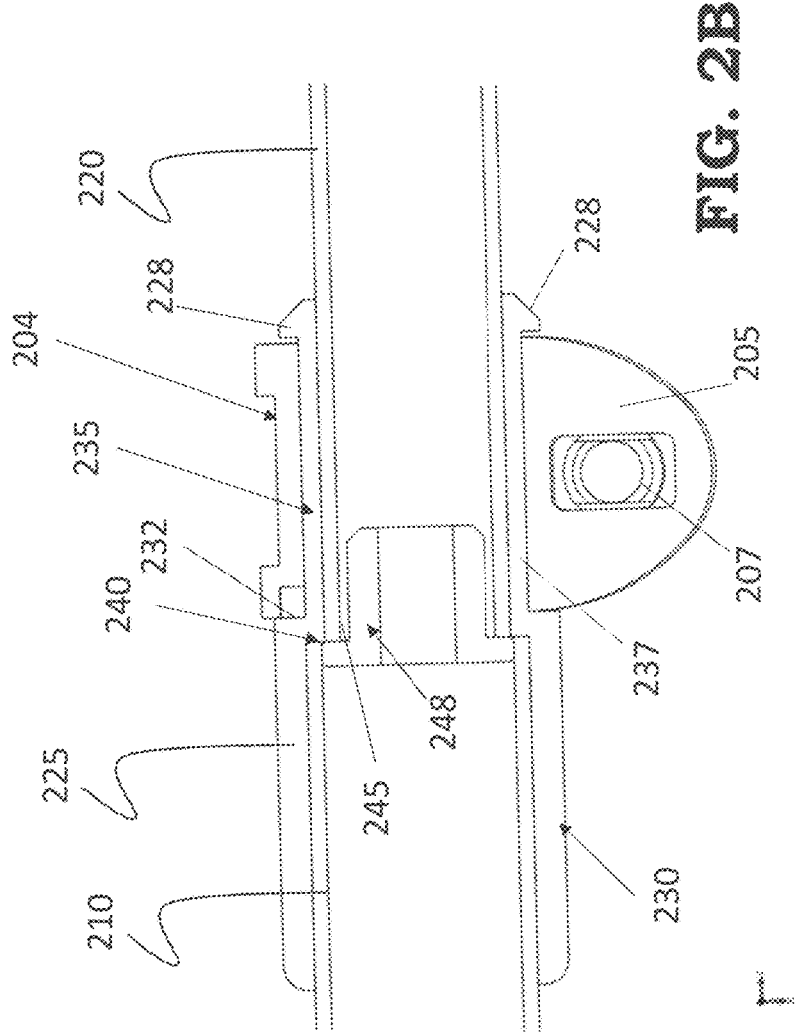
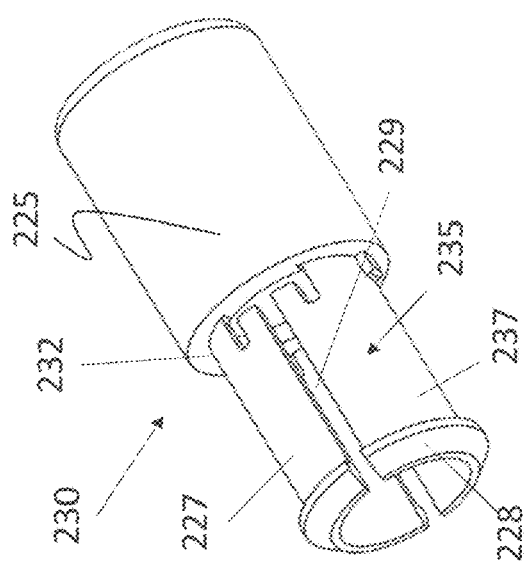

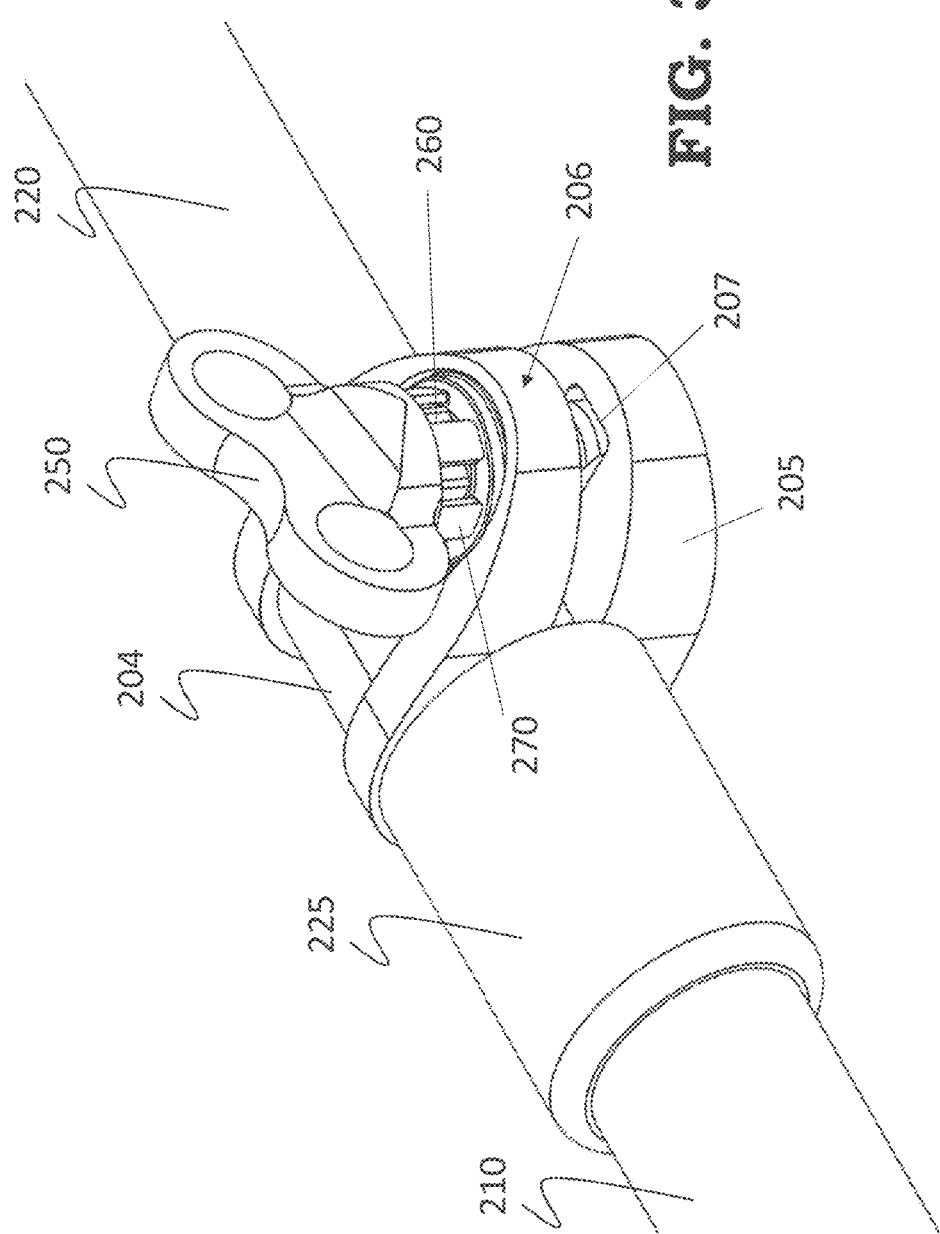

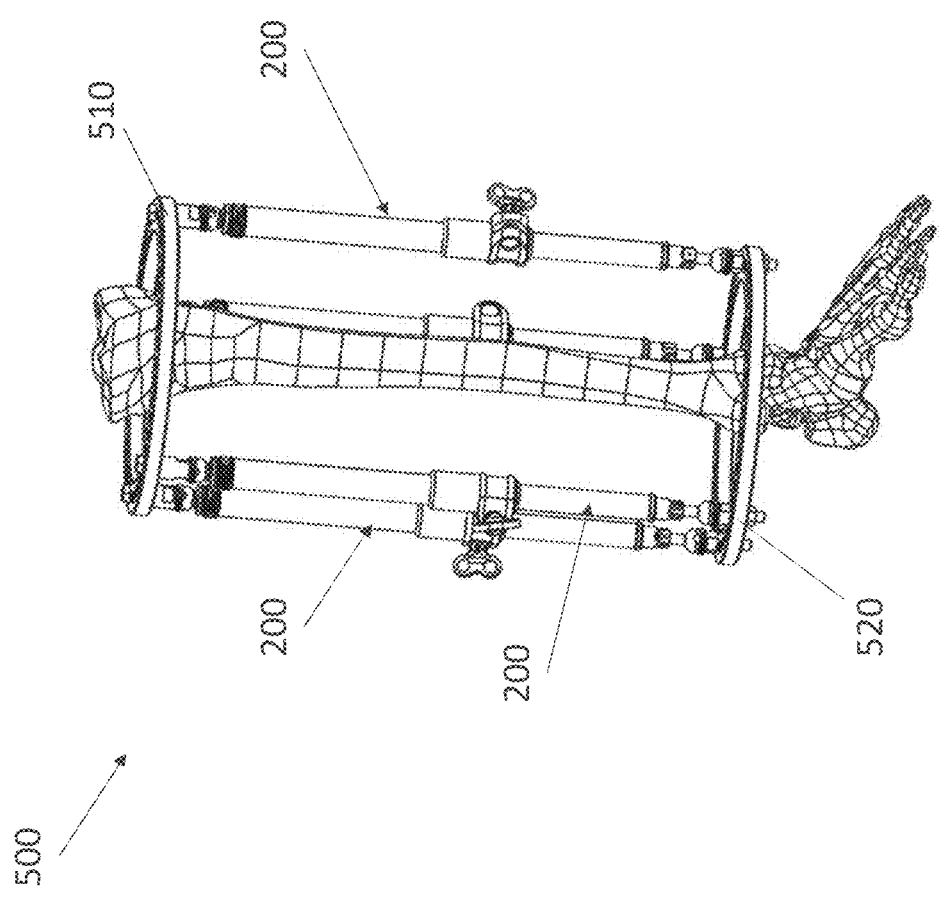

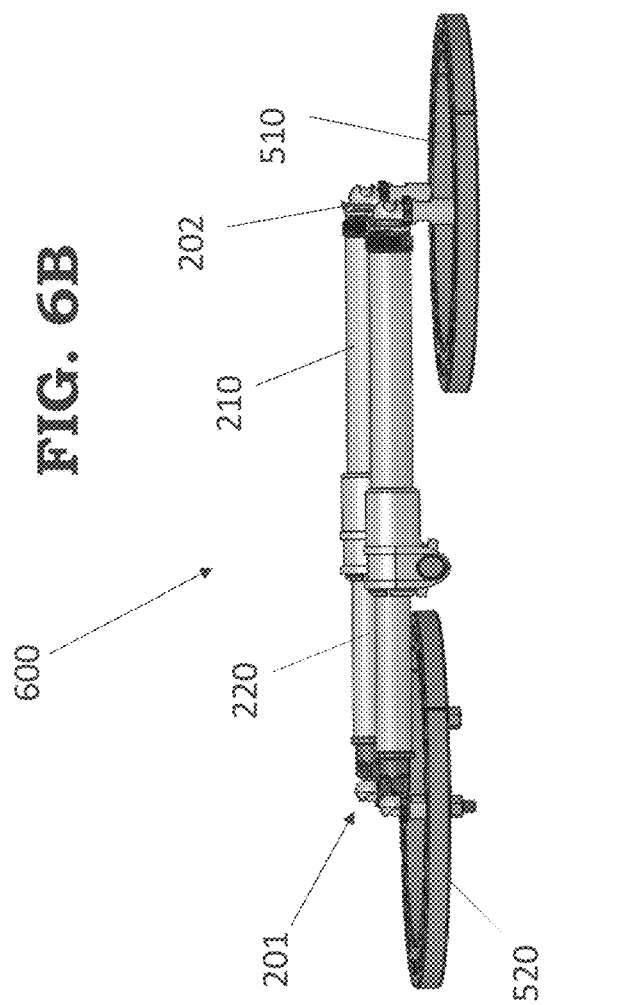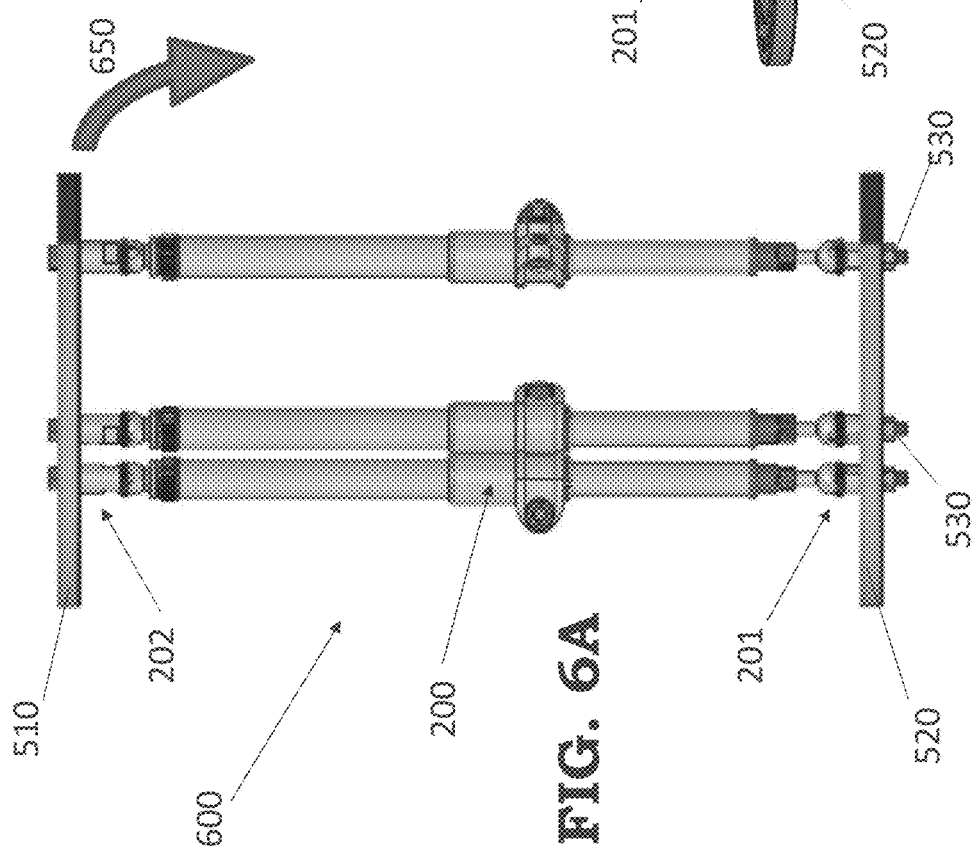

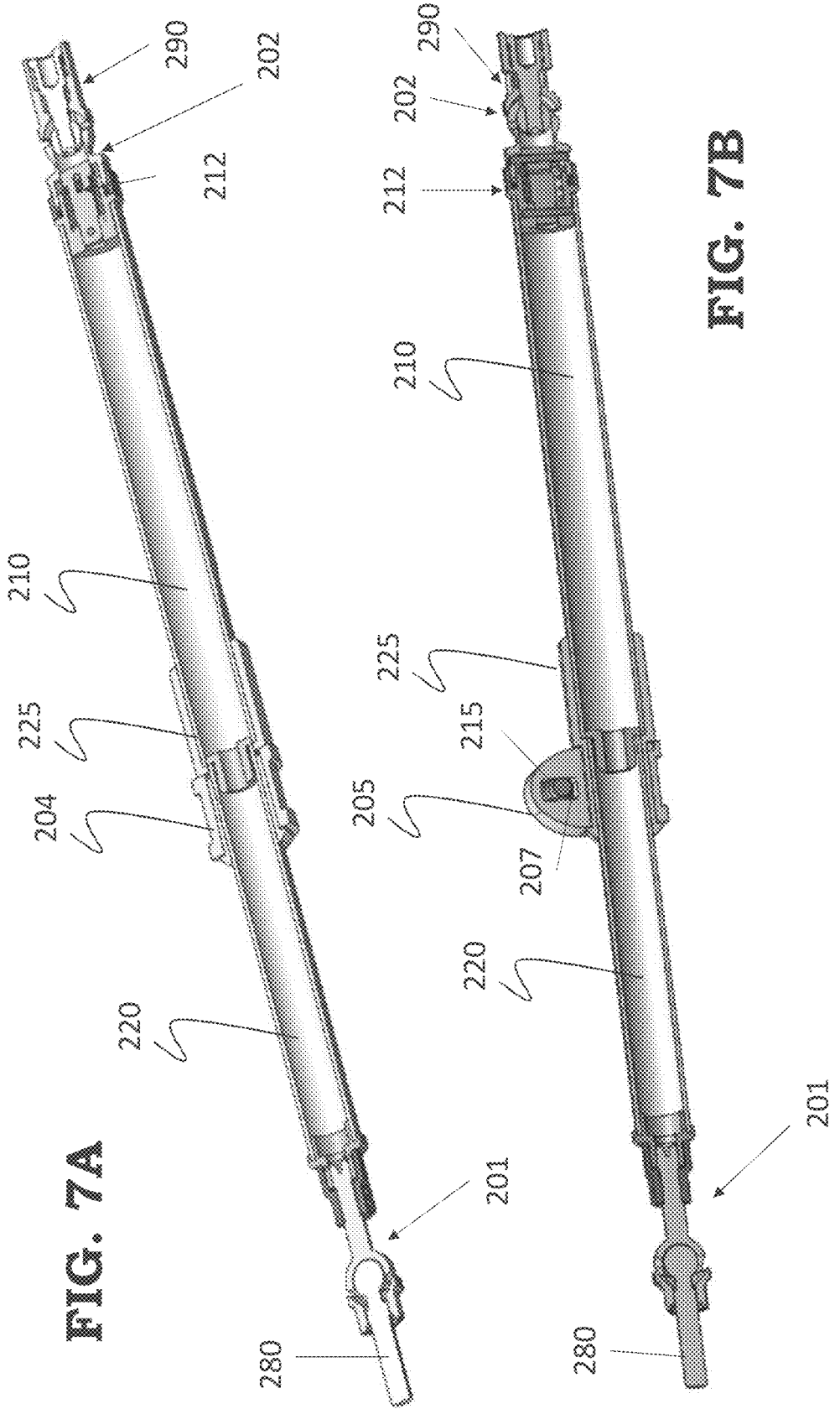

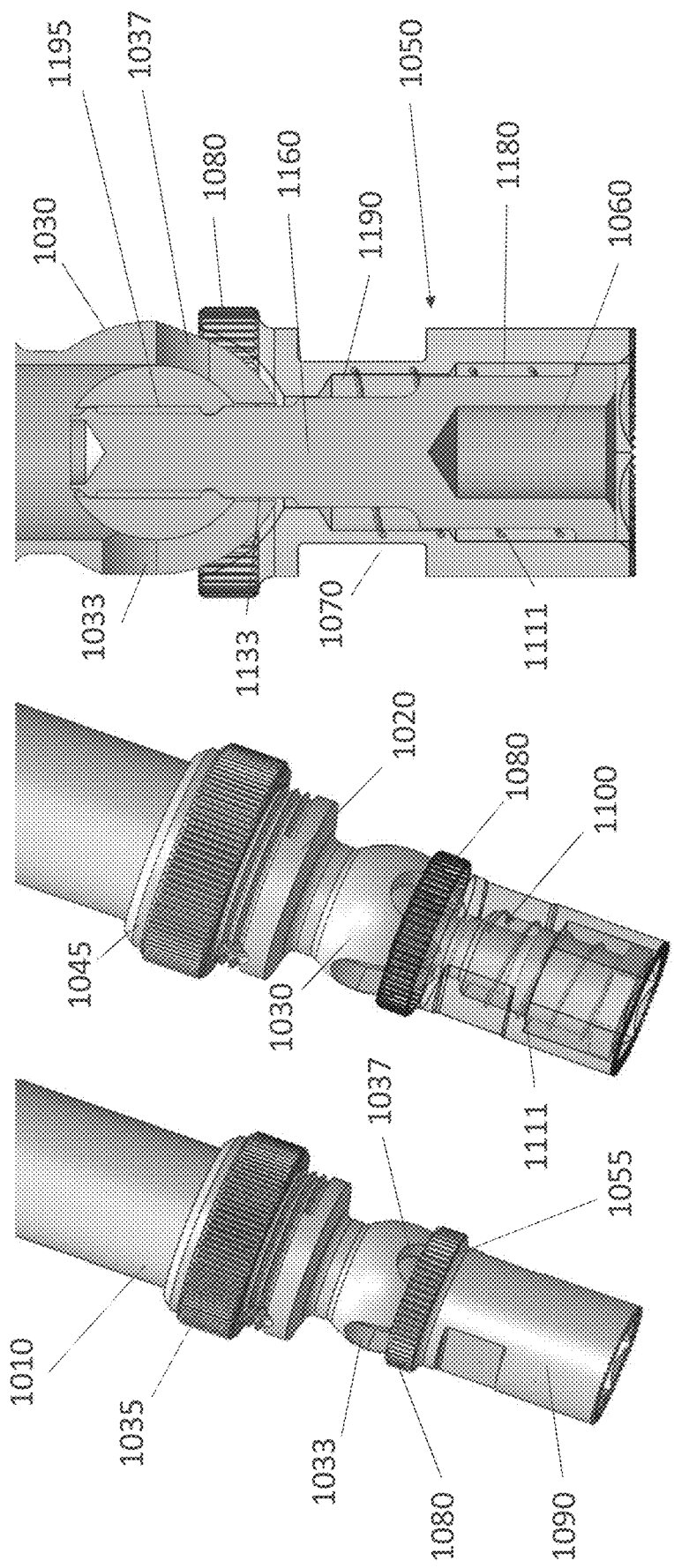

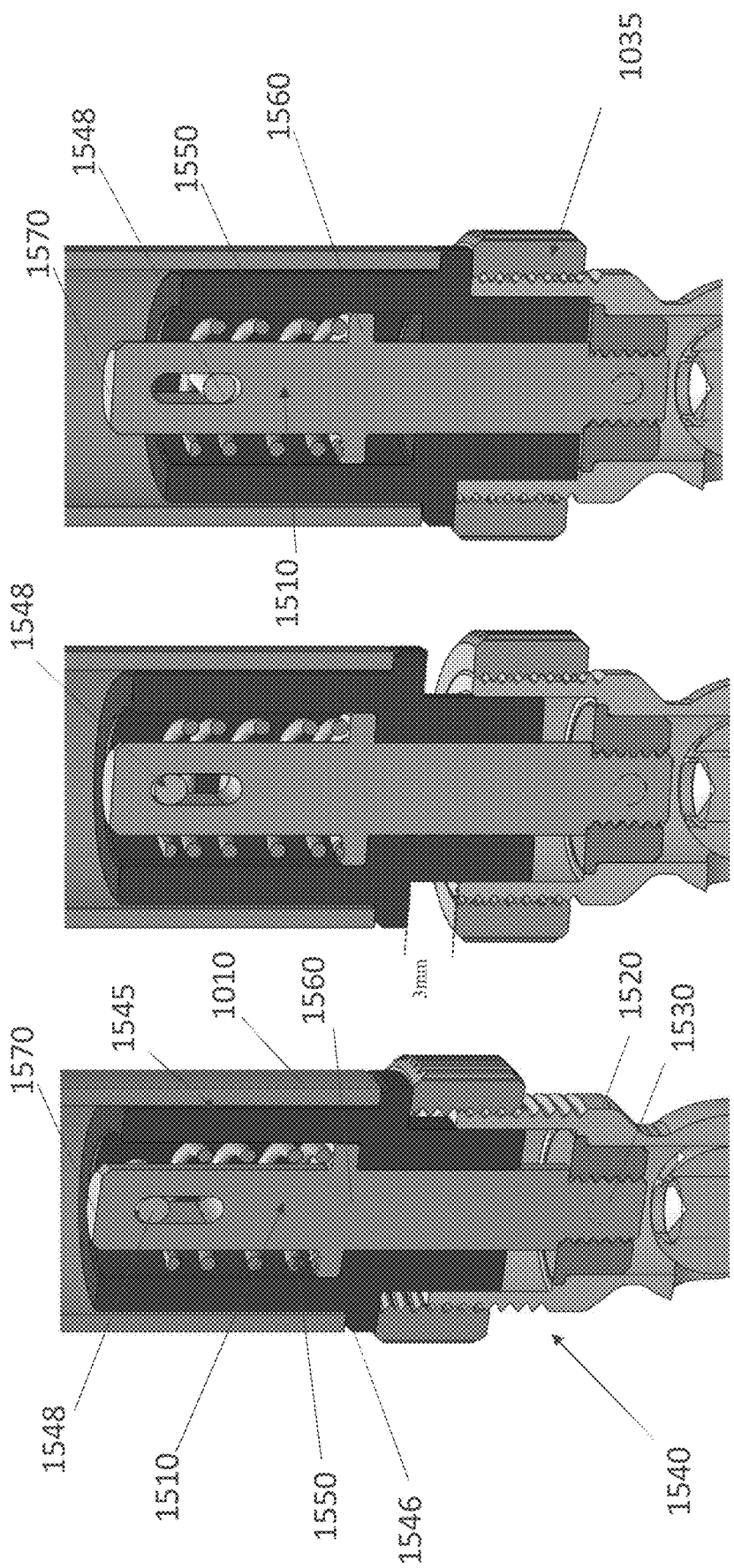

EXTERNAL FIXATION STRUT

BACKGROUND

The present disclosure relates to an improved structure for external fixation systems and devices and, more particularly, to improved external fixation struts.

The present invention is described in connection with external fixation devices and specifically connection struts and rods. Generally speaking, external fixation devices are commonly used in a variety of surgical procedures including limb fractures, limb lengthening and deformity correction. The process involves a rigid framework comprising several rings or arches that are placed externally around the limb and attached to bone segments using wires and half pins inserted into the bone segments and connected to the related section of the external rigid framework.

Rings of the rigid framework located opposite to one another are interconnected by either threaded and/or telescopic rods directly or in conjunction with uniplanar or multiplanar hinges, which allows the surgeon to adjust position of the rings relative to each other longitudinally, rotationally, horizontally or angularly over a period of time.

For example, in limb lengthening, the bone is surgically divided into two segments and wires and half pins are inserted into bone segments above and below the surgical bone cut and attached to rings of a rigid framework interconnected by struts or telescopic connection rods.

For limb lengthening, the opposite rings are interconnected directly by at least three or four threaded or telescopic rods that are regularly adjusted in length and allowed for gradual separation of bone segments longitudinally.

The rigid framework is used to gradually push the two bone segments apart longitudinally over a period of time (for instance, one millimeter a day). This allows the bone to gradually form in the gap between bone segments created by this distraction technique. Once the desired amount of lengthening is achieved (e.g., 5-6 cm), the external apparatus is stabilized into a fixed position and left on the bone segments until complete mineralization of the newly formed bone (e.g., 3-6 months, depending on the nature of pathology and amount of lengthening).

Similarly, in deformity correction, the bone is surgically divided (usually at the apex of the deformity) into two segments and wires and half pins are inserted into bone segments above and below the surgical bone cut and attached to rings of a rigid framework. In this case also opposite rings of the rigid framework are connected together by threaded rods with attached hinges and angular distractor that is used to gradually push the two bone segments apart angularly over a period of time.

Prior Art

One common fixation device is a circular metal structure known as the Ilizarov Apparatus. The Ilizarov apparatus, when used for limb lengthening or deformity correction, consists of several rings or arches that are placed externally around the limb and attached to surgically separated bone segments using wires and half pins. For angular deformity correction, the opposite rings of the Ilizarov apparatus are connected by a pair of hinges that provide an axis of rotation for bone segments and an angular distractor that gradually pushes two rings and associated bone segments apart.

Another common external fixation device is known as Taylor Spatial Frame, which is a hexapod type external fixation device based on a so-called Stewart platform but shares many components and features of the Ilizarov apparatus.

The Taylor Spatial Frame comprises two external fixation rings attached to bone segments by wires and half pins and connected together by five or six telescopic struts with multi-planar hinges located at both ends of the struts. Each strut may be lengthened or shortened as necessary to either pull two interconnected ring segments towards each other or push them apart.

Each strut of the Taylor Spatial Frame has a threaded rod partially disposed inside of a hollow shaft, and the hollow shaft includes an adjustment nut that mates with the threaded rod. However, effecting a rapid strut length adjustment or a gradual strut length adjustment to the length of the strut is time consuming and an exchange of the struts for longer ones during the treatment is often required.

Additionally, the replacement or removal of a strut from the Taylor Spatial Frame during the course of treatment is impossible without using external support or other stabilization mechanism to support the rest of frame since if one strut is removed from the frame, it would become unstable and collapse.

Other examples of fixation devices of this kind are commercially known as TrueLok and Sheffield, the last one being shown in FIG. 1 with the reference number 100.

Those solutions are frequently used for solving bones trauma situations for which it is very important for the surgeon to quickly reduce the fracture and to check the result of the reduction by a radiography with X-ray.

Both the above-mentioned products allow mounting struts having the possibility to be quickly connected to the corresponding rings so to free quickly the second ring with respect to the first one. This easy mounting system allows reducing and stabilizing the fracture in a relatively short time and further allows to regulate the relative inclination between the rings, Both types of products have however some drawbacks.

Firstly, the struts represent an obstacle in any X-ray picture often hiding the fracture visibility to the surgeon.

Secondly, while being relatively easy to mount, the known solutions require a relatively long time to be assembled and to be positioned on the patient also because the struts have an intrinsic weight that render uncomfortable the application on the patient.

Furthermore, the transport and storing of those known external fixators is always complex because of their size and encumbrance.

The technical problem underlining the present invention is that of providing a new strut for external fixator and a new fixator structure having functional and structural features overcoming the drawbacks affecting the prior art solution.

A main aim of the improved external fixator strut of the present disclosure is that of improving the visibility for the surgeon of the fracture site while allowing an easy axial movement of the strut for a possible micrometric dynamization.

SUMMARY OF THE INVENTION

The solution idea at the basis of the present disclosure is that of realizing the main portion of the rings interconnecting struts with a radiolucent material taking advantage of the join portions to host the micrometric regulation of the struts length.

According to such a solution idea the technical problem underlining the invention is solved by an improved external fixator strut comprising:

an elongated body comprising a first and a second hollow tubular shaft;

opposite connectors respectively coupled to an end portion of the first or the second shaft and each including a ball and socket joint;

one shaft having an internal diameter that is slightly larger than the external diameter than the other shaft to host internally the other shaft in a slidably and telescopic manner;

said first and second shafts of the strut being realized by a synthetic radiolucent plastic material;

a clamp element provided in proximity of overlapping ends of the first and second shaft for providing a fast gripping action stopping the telescopic sliding of one shaft inside the other shaft;

a manually operated fixation element acting on the clamp element for exerting said fast gripping action.

Various embodiments of an improved external fixation strut are included in this disclosure. In one embodiment, the external fixation strut includes:

a sleeve provided around the central portion of the strut where the first and second shaft overlaps; and a clamp band around said sleeve and including opposite and facing gripping portions at least one of them having a central threated hole receiving the threaded shaft of a clamping bolt. The clamping bolt has a head coupled to a removably manual operating key.

Also included in the present disclosure are various embodiments for a fixation system including at least a first and a second fixation ring and/or at least a fixation arch interconnected by some fixation struts wherein at least one of said fixation struts comprises:

an elongated body comprising a first and a second hollow tubular shaft;

opposite connectors respectively coupled to an end portion of the first or the second shaft and each including a ball and socket joint;

one shaft having an internal diameter that is slightly larger than the external diameter than the other shaft to host internally the other shaft in a slidably and telescopic manner;

said first and second shafts of the strut being realized by a synthetic radiolucent plastic material;

a clamp element provided in proximity of overlapping ends of the first and second shaft for providing a fast gripping action stopping the telescopic sliding of one shaft inside the other shaft;

a manually operated fixation element acting on the clamp element for exerting said fast gripping action.

Moreover, in the above fixation system each strut comprises opposite male and female connectors each including a ball-and-socket joint allowing an angular movement of the corresponding strut with a spherical angle up to at least 90° for folding the fixation system for packaging and transportation purposes.

BRIEF DESCRIPTION OF THE DRAWINGS

For a more complete understanding of the features and advantages of the present disclosure, reference is now made to the detailed description of the disclosure along with the accompanying figures and in which:

FIG. 2A is perspective view of a component of the external fixation strut of the present disclosure;

FIG. 2B is a cross section view of the component shown in FIG. 2A as mounted on the external fixation strut of the present disclosure;

FIG. 3 is a schematic and perspective view of the central portion of the strut of the present disclosure;

FIG. 5 is a perspective view of one embodiment of an external fixation system including struts realized according to the present disclosure;

FIG. 6A is another perspective view of a further embodiment of an external fixation system including at least three struts realized according to the present disclosure;

FIG. 6B is a perspective view of the embodiment of FIG. 6A in a folded configuration;

FIGS. 7A and 7B show cross-sectional views of the external fixation strut of the present disclosure taken from opposite point of views, respectively;

FIG. 12A is another perspective view of the female connector of FIG. 10;

FIG. 12B is a perspective view of the female connector of FIG. 10 wherein it is visible an internal spring-loaded mechanism;

FIG. 12C is a slightly enlarged cross-sectional view of the female connector of FIG. 12B;

FIGS. 15A, 15B and 15C show enlarged cross-sectional views of a further embodiment of the female connector of the present disclosure in different configurations, respectively.

DETAILED DESCRIPTION

While the manufacturing and using of various embodiments of the present disclosure are discussed in detail below, it should be appreciated that the present disclosure provides many applicable inventive concepts that can be embodied in a wide variety of specific contexts. The specific embodiments discussed herein are merely illustrative of specific ways to make and use the disclosure and do not delimit the scope of the disclosure.

Figure 1:
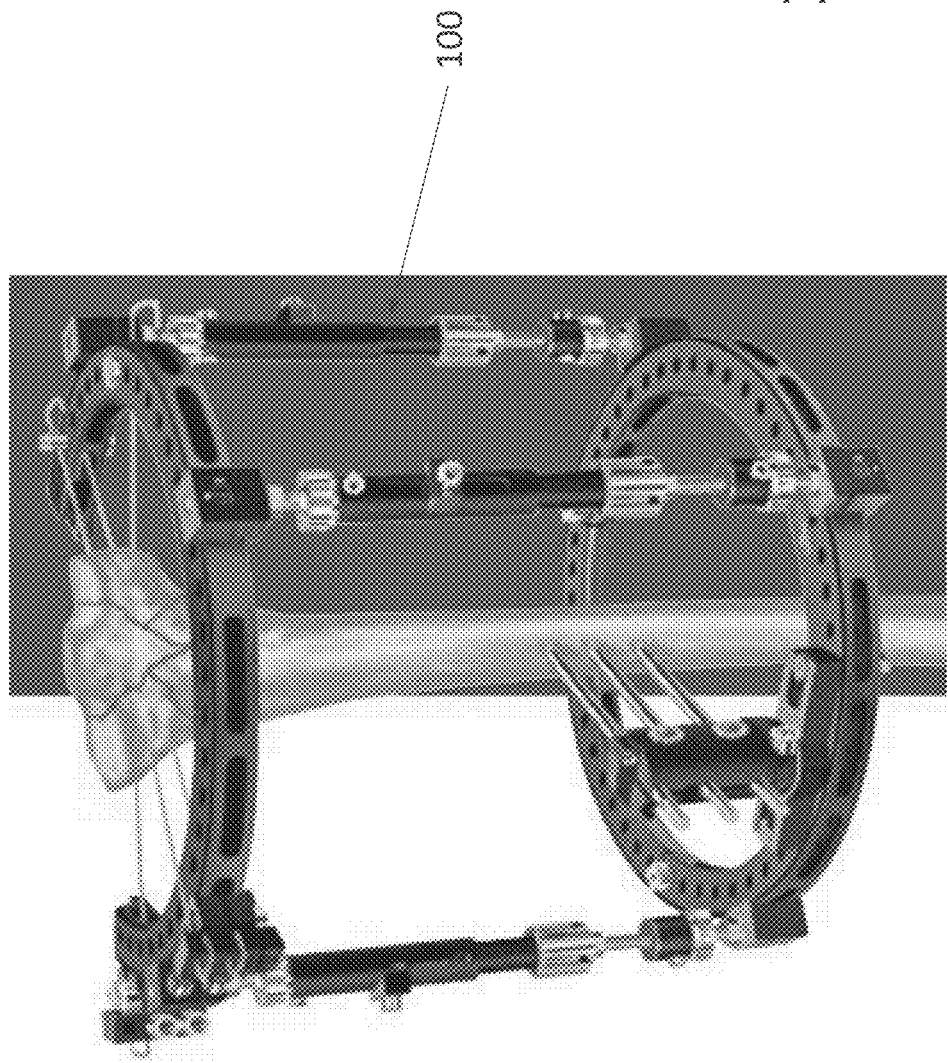
FIG. 1 is a perspective view of one embodiment of an external fixation system including struts realized according to the prior art.
Figure 2:
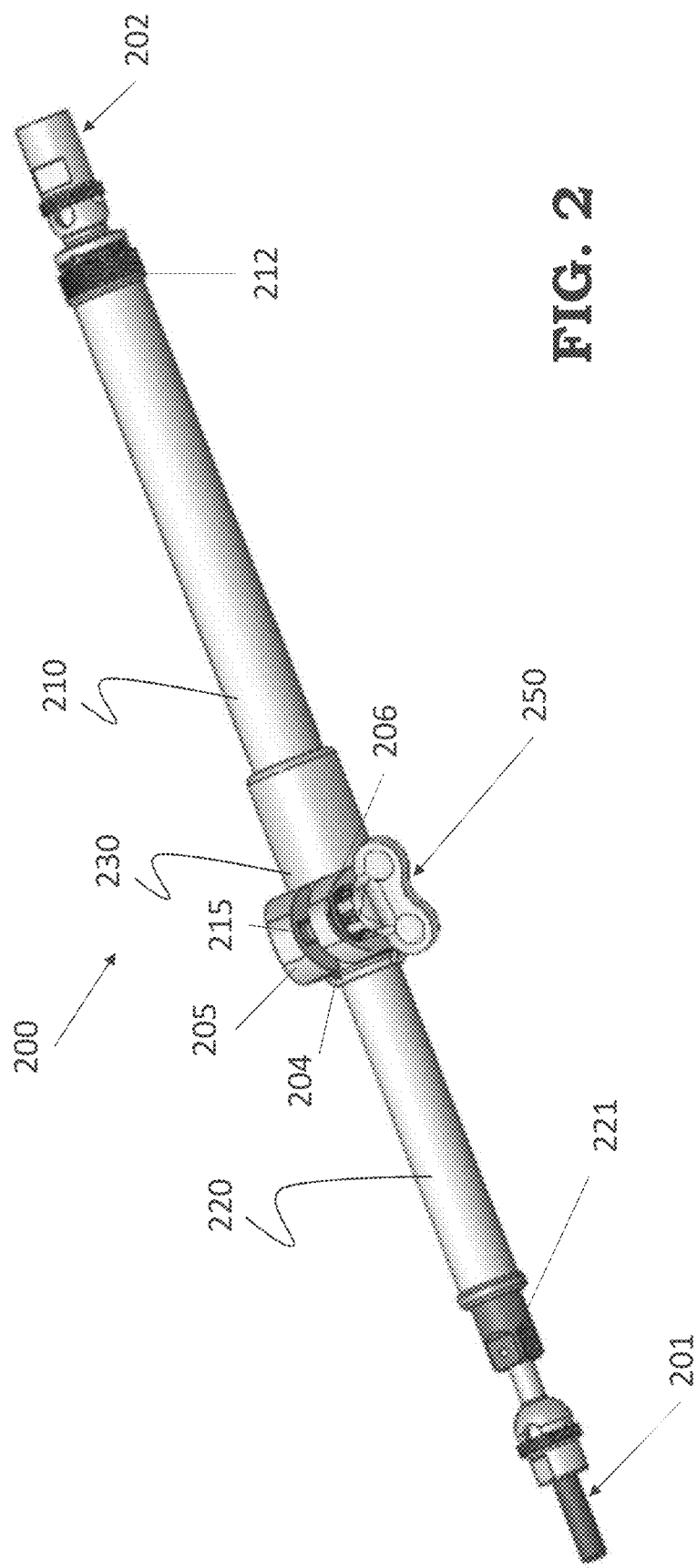
FIG. 2 is a schematic and perspective view of an embodiment of the external fixation strut of the present disclosure.

FIG. 2 shows a schematic view of an improved external fixation strut 200 according to the present disclosure having an elongated shape with opposite ends provided with connectors 201, 202 configured to be attached to a respective fixation ring or arch of an external fixator.

The rings of the external fixator to which the strut 200 is attached are shown in another figure that will be disclosed later.

The strut 200 has a main elongated body formed by a couple of hollow tubular shafts 210 and 220 which are aligned and coaxial. In embodiments of the present disclosure these shafts have cylindrical shape but other shapes may be adopted.

In the exemplary embodiment disclosed herein, the first shaft 210 has an internal diameter that is slightly larger than the external diameter than the second shaft 220 so that the second shaft 220 can be slidably hosted internally to the first shaft 210. In other words, the second shaft 220 may slide along the internal cavity of the first shaft 210.

This dimensional relationship between the first 210 and the second shaft 220 confers a telescopic configuration to the ensemble of the strut 200 that may be regulated in its length according to the needs of keeping the interconnected rings in a predetermined relative spatial relationship.

The shafts 210 and 220 of the strut 200 are realized by a synthetic plastic material that is radiolucent, i.e. transparent to X-ray radiation.

Just as a possible example these shafts may be realized with a techno-polymeric material for instance with PEEK (Polyetheretherketone). This techno-polymer is characterized with excellent thermal and chemical resistance; moreover, it presents good tribological, mechanical and dielectric properties which make it a good substitute for metallic materials since it supports sterilization cycles and is resistant to ionizing radiations.

A sleeve 230 is provided around the central portion of the strut 200 where the first 210 and second shaft overlaps or, better, in proximity of overlapping ends of the first and second shaft.

This sleeve 230 presents a recessed portion hosting a clamp band 204 having opposite and facing gripping portions 205, 206 that are forced to get one closed to the other by the action of a removably manual key 250, for instance a butterfly key. At least one of said gripping portions 205, 206 has a central threated hole 207 receiving a threaded shaft 215 of a clamping bolt 260. This clamping bolt 260 has a head coupled to the removably manual operating key 250.

More specifically, said manual key 250 may be structured as a knob or butterfly wrench that may be manually operated for tightening bolt forcing the two portions 205, 206 to get one closer to the other. The threaded shaft 215 is part of the bolt 260 having a recessed head and the manual key 250 is mechanically coupled to such a bolt 260 in a removable manner.

By acting on the butterfly wrench 250 an operator may stop the axial relative movement of one shaft 220 sliding inside the other shaft 210, thus regulating the axial main extension of the strut 200. This action is performed as a manual fast pre-closing of the telescopic stroke of strut 200.

The butterfly wrench 250 is removably associated to one 206 of the two facing gripping portions 205, 206 and may be removed leaving exposed the recessed head of the bolt 260 that may receive and host a key or tightening tool, as will be disclosed later in more detail with respect to another figure.

The external fixation strut 200 of the present disclosure has connectors 201, 202 including ball and socket joints that are associated to its opposite ends and can be attached to the outer or inner surface of a fixation ring or arch. These ball and socket joint connectors 201, 202 are respectively associated to male and female final connectors 280, 290 for a faster connection to a corresponding ring of the ring fixator.

At least one 201 of those ball joints connectors 201, 202 is housed in an adjustment mechanism 212 that allows for an independent rapid and gradual fine dynamization adjustment in length of the strut 200, as we will see in the following parts of this description.

The adjustment mechanism 212 may be considered an on-off dynamization section allowing the surgeon to pass from a rigid strut, with no movement under load, to an elastic strut with an axial up to at least 3 mm. The dynamization is achieved by means of a deformable element, for instance an elastic element like a spring housed inside a terminal section of a shaft, in particular a female connector. Two alternative embodiments of the dynamization mechanism 212 will be later disclosed.

FIG. 2A shows a perspective view of a component of the external fixation strut 200 of the present disclosure. More specifically, this component is the sleeve 230 provided around the overlapping internal ends of the first and second shafts 210, 220.

The sleeve 230 is structured with a first sleeve portion 225 having an internal diameter corresponding substantially to the external diameter of the first shaft 210 and a second sleeve portion 235 having an internal diameter corresponding substantially to the external diameter of the second shaft 220.

The first and second sleeve portions 225 and 235 are formed integrally as a single piece construction.

More specifically, the second sleeve portion includes two facing semi-tubular wings 227 and 237 projecting from the first sleeve portion 225 and separated one from the other by an air gap 229. There two tubular wings 227, 237 have their internal surfaces faced one to the other to form substantially the second sleeve portion 235 that appears open longitudinally along the opposite air gaps 229 and has a smaller diameter if compared to the diameter of the first sleeve portion 225.

The smaller diameter of the second sleeve portion 235 produces a radial step 232 between the second and first sleeves 235, 225 where they are linked.

A collar 228 is provided at the free end of each tubular wing 227 and 237. The collar 228 from one side and the radial step 232 from the other side define with the tubular wings 227 and 237 an annular space wherein the clamp band 204 is hosted.

FIG. 2B shows a cross sectional view of the sleeve 230 mounted on the improved external fixation strut of the present disclosure.

From this sectional view it may be appreciated that the first sleeve portion 225 if fixed around and on an internal end 240 of the first shaft 210 while the other sleeve portion 235 is abutting against such an internal end 240 in correspondence of the radial step 232.

The second shaft 220 has the internal end 245 faced to the internal end 240 of the first shaft 210 and slidable inside the first shaft in a telescopic manner. The internal end 245 of the second shaft is closed by a cap 248 that may be considered the end of stroke.

The clamp band 204 is hosted in the annular space or recess of the second sleeve 235 between the radial step 232 and the collar 228.

In this figure it is visible one gripping portions 205 of the clamp band 204 with the central threated hole 207 for receiving the threaded shaft of the butterfly wrench 250.

A tight pressure around the second sleeve 235 is obtained by the clamping action performed by the clamping band 204 when the gripping portions 205 and 206 are forced to get closer by the butterfly wrench 250. This clamping action performs a fast gripping action stopping the telescopic sliding of the second shaft 220 inside the first shaft 210.

FIG. 3 shows another perspective view of one embodiment of the external fixation strut of the present disclosure for an external ring fixation device. The external fixation strut 200 is shown in its central portion wherein the two shafts 210 and 220 overlaps in a telescopic manner.

The sleeve portion 230 is wrapping the central portion of the strut 200 where the first 210 and second coaxial shaft 220 overlaps.

The clamp band 204 is hosted and provided in the recessed portion of the second sleeve portion 235 with its facing gripping portions 205, 206 projection laterally from the sleeve portion 230.

The central threated hole 207 of the gripping portions receives the threaded shaft of tightening bolt 260 having a polygonal head, for instance a hexagonal head.

The butterfly wrench 250 is overlapped to the head portion of the bolt 260 with projecting flanges 270 regularly disposed in a polygonal layout substantially corresponding to the faces of the polygonal head of the bolt 260.

Obviously, another configuration may be adopted. For instance, the wrench 250 may be structured with a polygonal hole fit or put on the polygonal head of the tightening bolt 260.

In other words, the butterfly wrench 250 is a user adaptor for the tightening bolt 260 allowing the user to exert a faster and stronger manually operated gripping action forcing the two portions 205, 206 to get closer one to the other through the threaded action of the bolt 260.

By acting on this butterfly wrench 250 an operator may stop the axial relative movement of one shaft sliding inside the other shaft, thus regulating the axial main extension of the strut 200.

Figure 4:
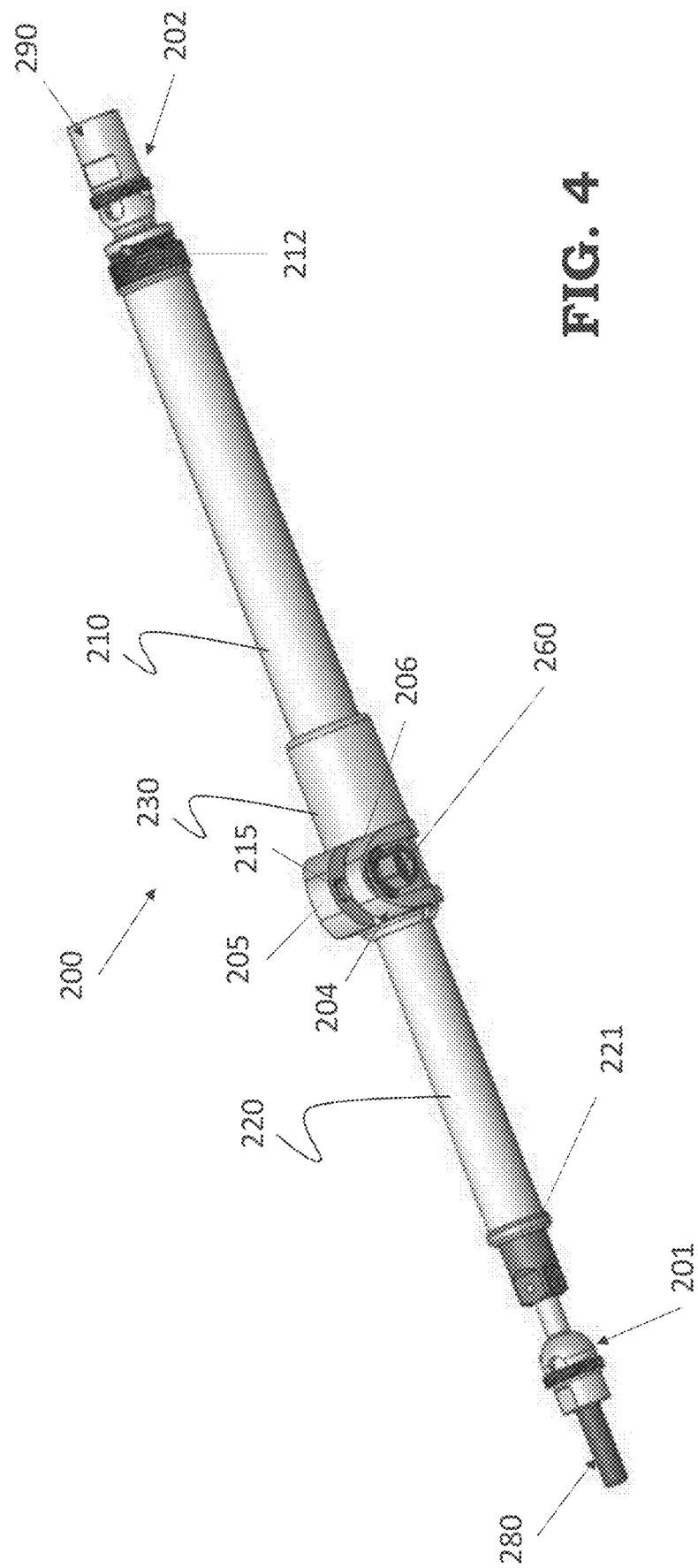
FIG. 4 shows another schematic and perspective view of the external fixation strut of the present disclosure in a different configuration.

FIG. 4 shows a schematic and perspective view of the external fixation strut 200 of the present disclosure wherein the butterfly wrench 250 has been removed after a manually pre-closing action of the telescopic stroke of the strut 200 without the need to access foreign keys. This is to reduce the time and complexity of the operation. At the end the wrench 250 is removed manually and the definitive locking is done with the help of a key.

Without the butterfly wrench 250 the bolt head is exposed and the adopted configuration may be tightened with the use of a key.

FIG. 5 is a perspective view of one embodiment of an external fixation system 500 including struts 200 realized according to the present disclosure.

The fixation system 500 includes at least a couple of fixation rings 510 and 520. As an alternative, at least one of those fixation rings may be a fixation arch (not shown) for instance in the distal portion of the fixation system 500.

The fixation rings 510 and 520 are interconnected through some fixation struts 200 as previously disclosed, for instance at least three or four struts. However, nothing prevents by adopting a system configuration including a larger number of struts, for instance six.

Each of the struts 200 is structured as disclosed in the previous passages of the present disclosure. However, for reasons due to needs of having at least one strut provided with a special dynamization function, it might be used at least a strut having a different configuration.

Said differently, the fixation system 500 may include at least one strut 200 according to the present disclosure.

Advantageously, the strut 200 are connected to the rings 510 and 520 through opposite connectors 201, 202; a male connector 201 and a female connector 202.

The connectors cooperate with holes (not shown) provided regularly along the rings or arches and are fixed to the rings or arches through fixation bolts 530.

Each connector is further associated to a ball-and-socket joint to allow an angular movement of the corresponding strut with a spherical angle up to at least 90° and a working angle up to at least 45°.

The angular freedom of the connectors 201 and 202 allow folding the fixation system 500 for packaging and transportation purposes.

Moreover, the system 500 may be structured in a pre-assembled configuration that is prepared in a sterilized environment and packed accordingly for a faster surgeon later use.

FIG. 6A shows a perspective view of a further embodiment of an external fixation system 600 including three struts 200 realized according to the present disclosure.

The struts 200 shown in this figure do not present the butterfly wrench 250 meaning that the telescopic length of the struts 200 has already been regulated and that the adoption of the opposite ball joints 201 and 202 allows folding the whole structure in the direction of the curved arrow 650 to obtain a substantially flat configuration of the fixation system 600.

Therefore, thanks to the possibility given by the angle of the ball joints up to 90° it is possible to have a pre-assembly of the fixation system including at least two rings and from two to four strut already assembled and folded. This configuration is supplied in a sterile package with reduced size.

FIG. 6B shows a perspective view of the embodiment of FIG. 6A in a folded configuration.

The junction elements 201 and 202 allow up to 90° of angulation and it is possible to lead the two rings 510 and 520 with the connected struts 200 almost on the same plane, as shown in FIG. 6B.

The 90° angulation can be achieved both in female and male end thanks to a bigger slot on the junction elements that will be disclosed in detail hereinafter. The other slots remain the same of the current strut.

FIG. 7A shows a cross-sectional view of the external fixation strut of the present disclosure. The two shafts 210 and 220 overlaps in a telescopic manner and the sleeve portions 225, 227 wrap the central portion of the strut 200 where the first 210 and second coaxial shaft 220 overlaps.

The recessed portion 204 of the second sleeve portion 225 is provided for hosting the clamp band.

FIG. 7B shows another cross-sectional view of the external fixation strut of the present disclosure taken from opposite point of view.

In this FIG. 7B it is visible a gripping portion 205 having a central threated hole 207 receiving a threaded shaft 215 of the clamping bolt.

The dynamization mechanism 212 is associated to the female connector 202. However, an alternative reversed embodiment wherein the dynamization mechanism is associated to the male connector 201 cannot be excluded.

Figure 8:
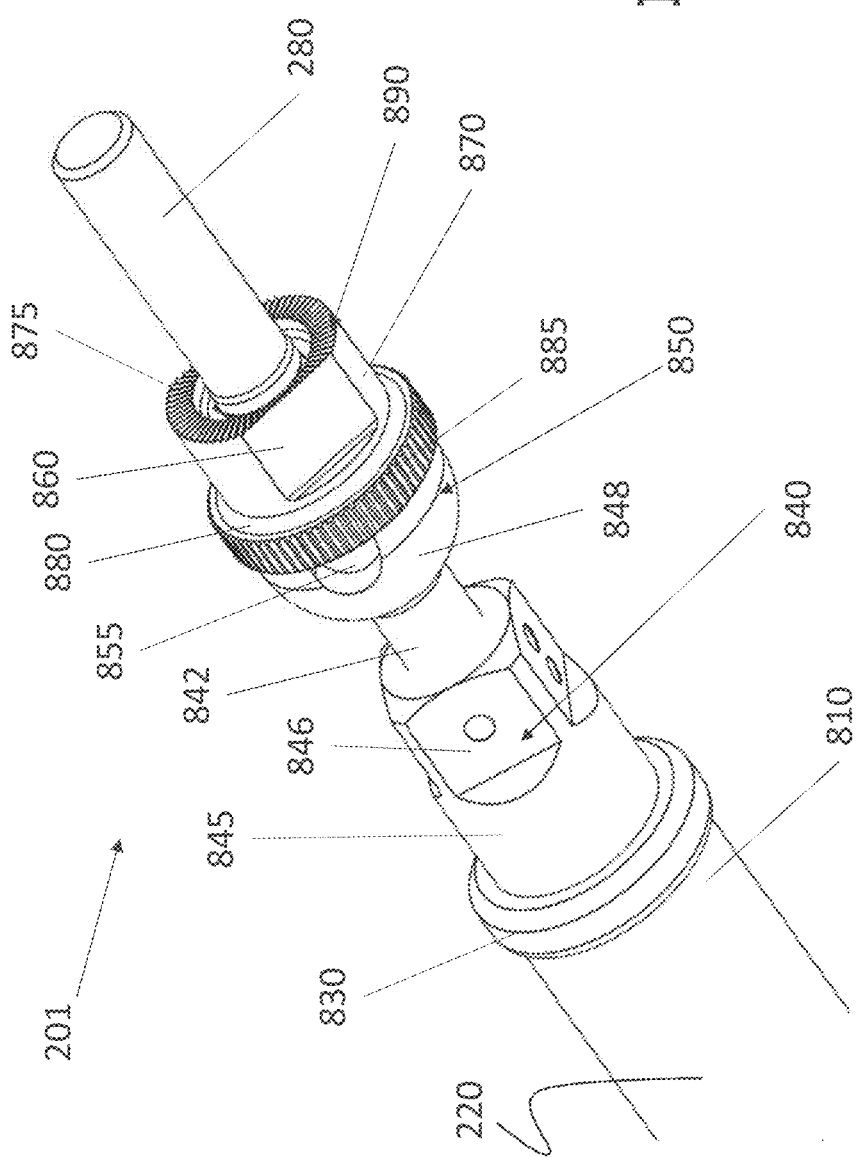
FIG. 8 is a perspective view of a male connector associated to one end of the external fixation strut of the present disclosure.

FIG. 8 is a perspective view of a male connector 201 associated to one end of the strut 200 according to the present disclosure.

More specifically, the male connector 201 is associated to one free end 810 of the second shaft 220 and comprises a couple of stages 840 and 850 coupled in a mechanical sequence. The first stage 840 is an interconnecting stage for a ball and socket joint stage 850 bringing a threaded rod 280 of the male connector 201.

The first stage 840 is connected to the end 810 of the second shaft and includes a support element 845 for a rod 842 having a terminal portion configured as a ball cage 848 for a ball-and-socket joint of the second stage 850.

The support element 845 is associated to a base portion 830 fixed to the free end 810 of the second shaft 220 and presents a central portion with at least two opposite flat surfaces 846 that have been provided for allowing the insertion of an operating key (not shown).

The rod 842 may be structurally independent from the support element 845 or may be integrally formed with such a support element. In the first case the rod 842 projects from a central hole of the support element 845 in order to be substantially coaxial with the second shaft 220.

The second stage 850 comprises a ball 855 for the ball-and-socket joint wherein the ball cage 848 represents the socket and a threated rod 280 integrally formed with the ball 855.

The more projecting portion of this threated rod 280 represents a male connection for one or the other of the fixation rings 510, 520 of the fixation system 500. More particularly, the threated rod 280 may be inserted in one of the holes normally provided in said fixation rings and then fixed by a fixation bolt 530.

A special closure cap 890 is fit on the threaded rod 280 and closes the socket portion of the ball and socket joint formed by the ball cage 848 and the ball 855.

This special closure cap 890 is formed by two cylindrical portions having different diameters. A first higher or thicker portion 870 provided with a couple of opposite flat surfaces 860 for allowing the insertion of an operating key (not shown).

This first portion 870 has a knurled or milled surface 875 for improving the adherence between the male connector 201 and the corresponding ring 510 or 520 of the fixation system 500.

A second smaller portion 880 of the closure cup 890 has a larger diameter and a knurled or milled peripheral surface 885 for allowing the manual rotation performed by an operator.

A more detailed explanation of the internal structure of the male connector 201 is reported in the following disclosure of FIG. 9 wherein parts and components having the same structure and functioning of the elements disclosed in FIG. 8 reports the same reference numbers.

Figure 9:
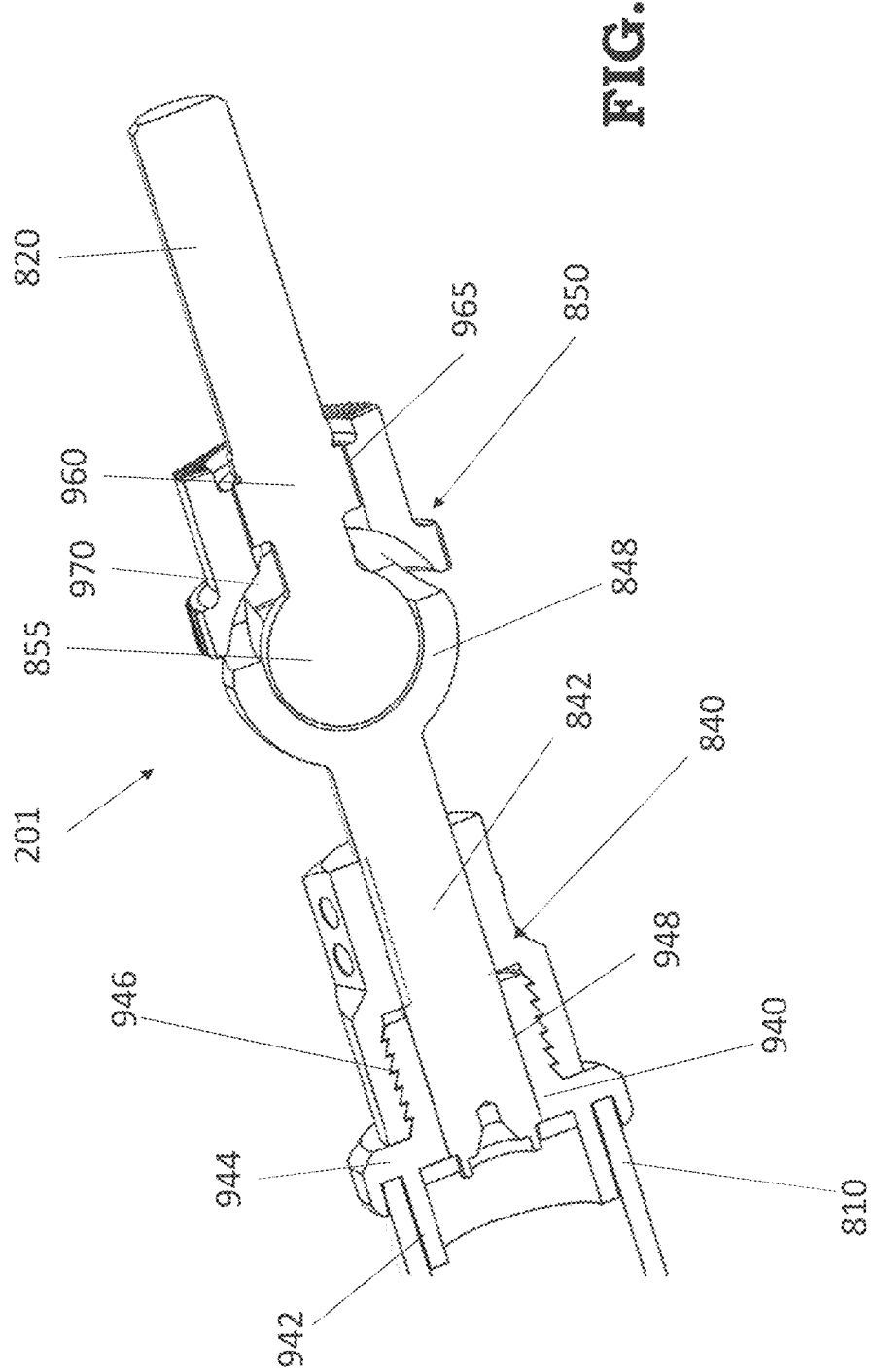
FIG. 9 is a cross sectional view of the male connector of FIG. 8.

FIG. 9 is a schematic and perspective view of a cross section of the male connector 201 already disclosed with reference to FIG. 8.

A first stage 840 is linked to the end 810 of the second shaft 220 and includes a special shaft terminal element 940.

This shaft terminal element 940 has a first portion 942 that is fitted with interference or fixed on the end 810 of the second shaft, in particular internally to such an end. A second intermediate portion 944 wraps as a peripheral collar the end 810 while a third extended portion 946 is provided to interconnect to the support element 845 of the interconnecting stage 840.

The second intermediate portion 944 corresponds to the base portion 830 shown in FIG. 8.

Moreover, the extended portion 946 is externally threaded and presents a passing hole 948 for hosting the rod 842 supporting the ball and socket joint stage 850.

The rod 842 passes through the hole 948 and through a further hole of the support element 845.

The support element 845 is screwed on the externally threaded part of the extended portion 946 abutting at the end of the stroke against the intermediate portion 944, i.e. the base portion 830.

However, the screwing action of the support element 845 may regulated in order to obtain a controlled micrometric axial movement of the whole strut 200 when connected to the opposite fixation rings 510, 520.

In other words, by action on the number of turns of the screwed coupling between the support element 845 and the externally threaded extended portion 946 it is possible to control with great precision the stroke of the whole strut 200 when mounted between the two rings 510, 520.

The ball cage 848 is the projecting portion of the rod 842 and represents the seat or socket of the ball and socket joint stage 850.

The ball 855 is formed in a one-piece construction with the threaded rod 280 that presents also an enlarged diameter 960 closer to the ball 855 and provided with an external treaded surface 965.

The special closure cap 890 is screwed on the external threaded surface 965 of rod portion 280 with enlarged diameter 960 up to the moment wherein the second smaller portion 880 of the closure cup 890 abuts against the ball cage 848.

From the cross section of FIG. 9 it may be appreciated that internal part of the closure cap 890 has an hemispheric shape 970 defining a sort of closure for the ball cage 848 and defining with the ball cage 848 a spherical chamber wherein the ball 855 of the ball and socket joint may angularly move.

Figure 10:
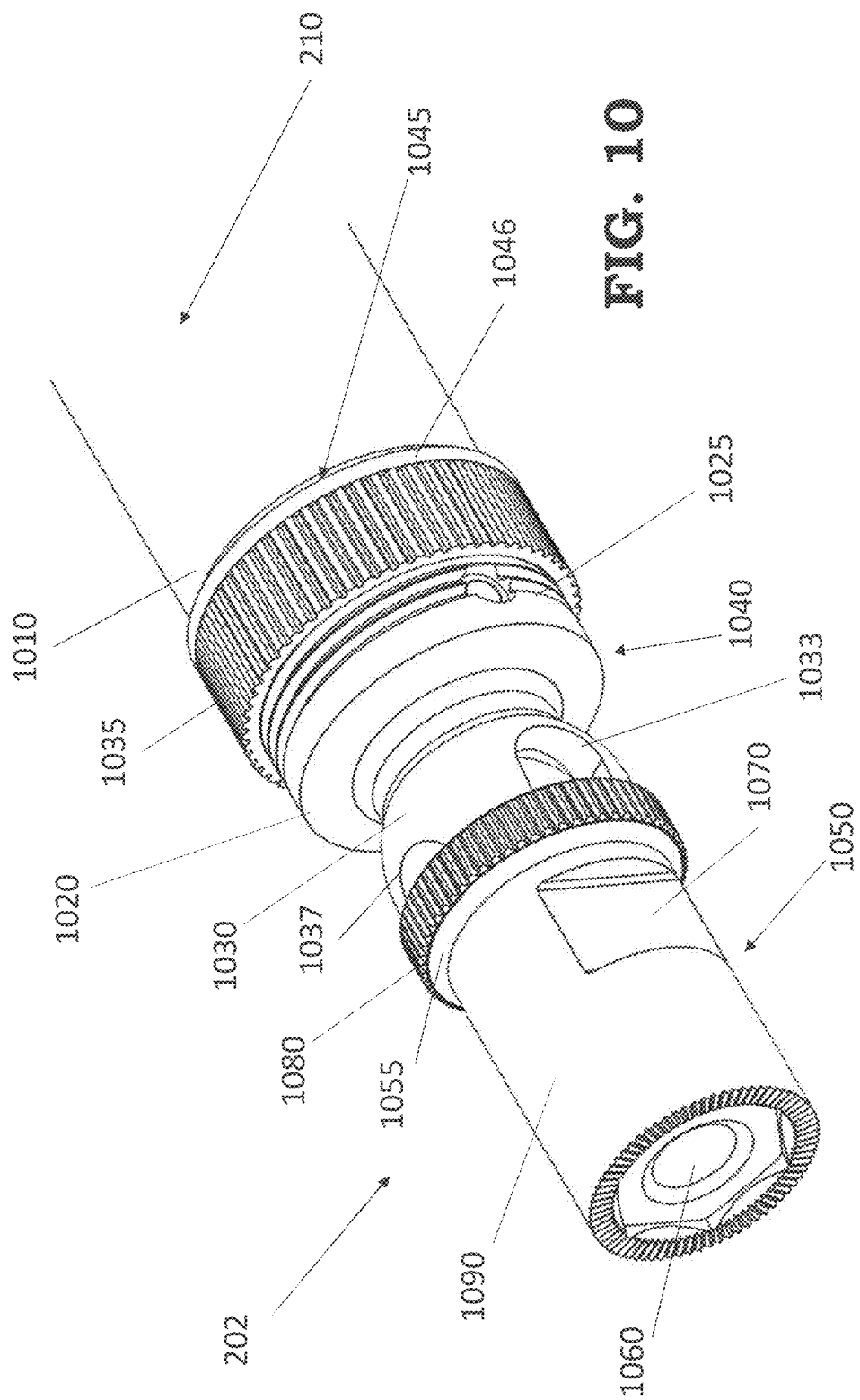
FIG. 10 is a perspective view of a female connector associated to one end of the external fixation strut of the present disclosure.

FIG. 10 is a perspective view of a female connector 202 associated to one end of the strut 200 according to the present disclosure.

More specifically, the female connector 202 is associated to one free end 1010 of the first shaft 210 and comprises a couple of stages 1040 and 1050 coupled in a mechanical sequence. The first stage 1040 is a joint stage for a final stage 1050 including a female element 1060.

The first joint stage 1040 is connected to the end 1010 of the first shaft 210 and includes a support element 1045 mounted on the end 1010 of the shaft 210 as a closure cap but coupled to a base portion 1020 of a ball joint 1030.

The support element 1045 has a closure collar 1046 abutting against the end 1010 of the shaft 210.

The base portion 1020 has an external threaded part 1025 and is connected to the support element 1045 by a threaded adjustment ring 1035. This ring 1035 is part of the adjustment mechanism 212 that will be disclosed in mode details with reference to the next FIG. 11 and has a knurled or milled peripheral surface for allowing a manual rotation performed by an operator.

Advantageously the adjustment ring is made with a reinforced plastic material transparent to X-ray radiation.

The ball joint 1030 projecting from the base portion 1020 has a plurality of regularly spaced apertures 1037, for instance four apertures. One 1033 of those apertures is larger than the others 1037.

The final stage 1050 of the female connector 202 has a more distal portion 1055 coupled to the ball joint 1030 and a proximal and final cylindrical portion 1090 including the female element 1060 that is internally threaded for receiving an interconnection bolt (not shown) for connecting one end of the strut 200 to a ring of the fixation system 500.

The proximal and final cylindrical portion 1090 is provided with opposite flat surfaces 1070 for the insertion of an operating key while the distal portion 1055 has an enlarged annular ferrule 1080 with a knurled or milled peripheral surface for allowing the manual rotation performed by an operator.

Figure 11A:
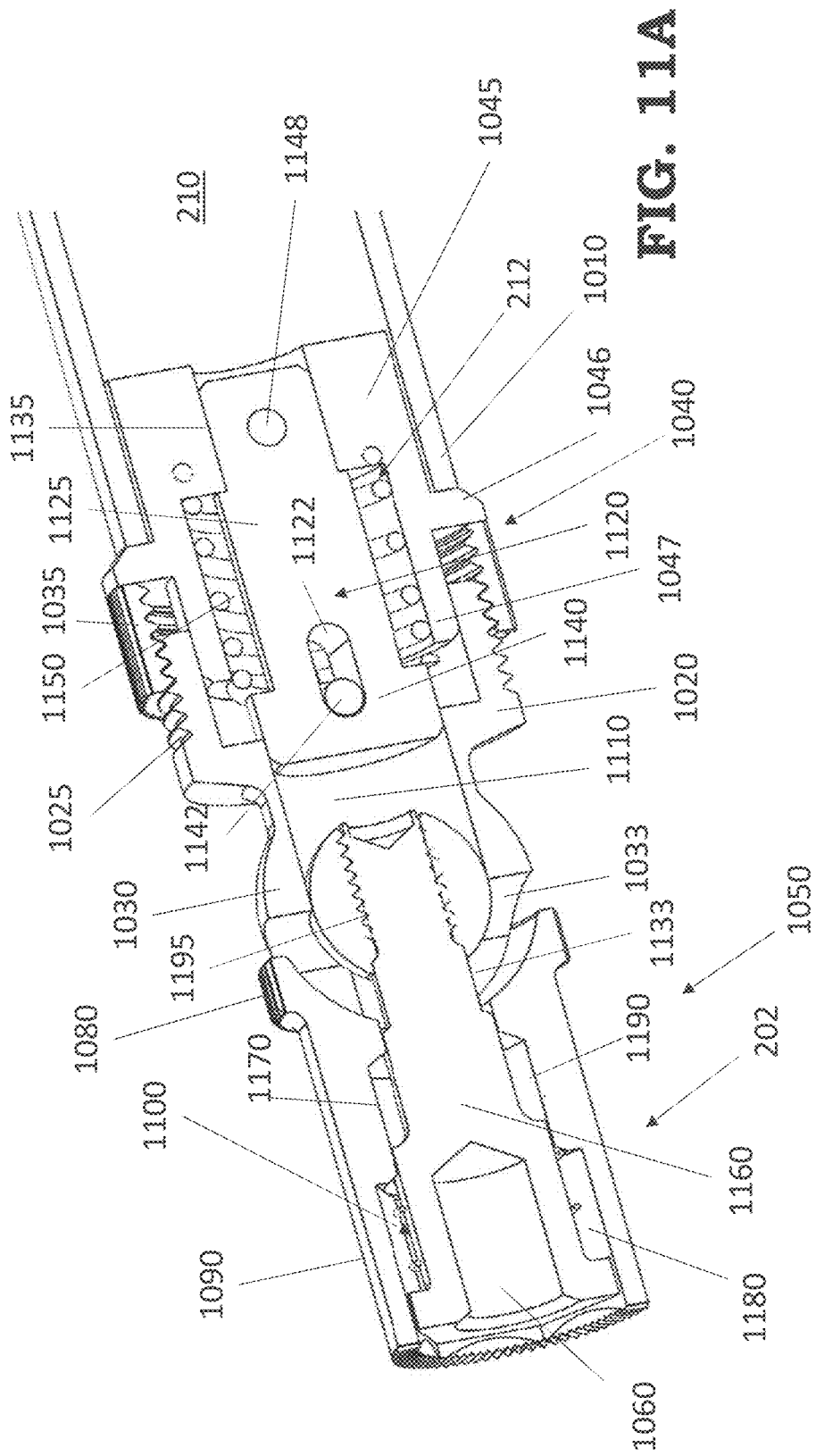
FIG. 11A is a cross sectional view of the female connector of FIG. 10.

FIG. 11A shows a cross sectional perspective view of the same female connector 202 of FIG. 10 but showing in more details the already mentioned adjustment mechanism 212 that allows for an independent rapid and gradual fine adjustment in length of the whole strut 200.

As usual, parts and components having the same structure and functioning already disclosed are identified with the same reference numbers.

From this cross sectional view it may be appreciated that the ball joint 1030 projects from the base portion 1020 that is externally threaded.

This special structure including the ball joint 1030 and its base portion 1020 is mounted on the support element 1045 fixed at the end 1010 of the shaft 210 and presents a passing hole 1110 hosting a pin 1120 having a T shape inner shaft 1125 sliding in a hole 1135 of the support element 1045 and an enlarged portion 1140 sliding along the passing hole 1110.

A first transversal pin 1148 is fixed with the support element 1045 and crosses the stem of the inner shaft 1125 in its distal portion.

The support element 1045 is realized by a synthetic plastic material transparent to X-ray radiation and may be considered as a plastic sleeve closing the end 1010 of the shaft 210 while at the same time providing the seat for a dynamization mechanism that will be disclosed hereinafter.

More specifically, the support element 1045 is structured as a sort of double sleeve with a portion inserted into the shaft end 1010, a collar 1046 abutting against the shaft end 1010 and a projecting portion 1047 supporting in a slidable manner the inner part of the base portion 1020 of the first stage 1040.

The T shaped inner shaft 1120 is advantageously realized by a radiolucent metal component, for instance Aluminium or, as alternative, a reinforced plastic material.

An elastic element 1150 is provided inside the support element 1045. More particularly, a spring 1150 is wrapped around the stem 1125 of the inner shaft 1120 inside the support element 1045 to exert an elastic action in cooperation with the screwing action of the threaded adjustment ring 1035 of the external threaded part 1025 of the base portion 1020.

A second transversal pin 1142 is fixed with the base portion 1020 and crosses the enlarged portion 1140 of the T shaped inner shaft 1120. This second transversal pin 1142 is slidable inside an elongated slot 1122 similar to a buttonhole formed centrally in the T shaped inner shaft 1120 and aligned along the main axis of the T shaped inner shaft 1120. A relative movement between the support element 1045 and the base portion 1020 of the first stage 1040 is accompanied by a corresponding relative movement of the second transversal pin 1142 inside the slot elongated 1122.

The following components: support element or plastic sleeve 1045, base portion 1020; threaded part 1025, threaded adjustment ring 1035, T shaped inner shaft 1120 and spring 1150 form all together the dynamization adjustment mechanism 212.

The dynamization mechanism 212 of this embodiment includes the T shaped inner shaft 1120 made in plastic material and assembled to the plastic support element 1045 together with the first transversal pin 1148 that is used to assemble the two plastic parts. The second transversal pin 1142 is used as mechanical stop for the compression of the spring 1150 and to avoid any accidental disassembling of the strut.

Acting manually on the threaded adjustment ring 1035 it is possible to regulate the excursion of the base portion 1020 with the ball joint 1030 with respect to the end 1010 of the shaft 210 and against the elastic action of the spring 1150. In this manner it is allowed a smooth and independent rapid and gradual fine adjustment in length of the whole strut 200 through this adjustment mechanism 212.

In a preferred embodiment this adjustment in length is of at least 3 millimeters.

The structure of the female connector 202 is completed by a spring-loaded mechanism 1100 provided in the final stage 1050 around the female element 1060.

More specifically, the female element 1060 of the female connector 202 is realized at the end of a rod 1160 slidable inside a tubular hole 1180 formed by a first and second coaxial tubular chambers 1180, 1190 having different diameters and realized internally to the final and proximal cylindrical portion 1090.

The rod 1160 has a distal portion 1195 that is threaded to be screwed in a corresponding seat provided in the ball joint 1030.

The spring-loaded mechanism 1100 includes a spring 1111 that is hosted inside the first tubular chamber 1180 and wraps the more proximal portion of the rod 1160 where the female element 1060 is formed.

The rod 1160 is extended through an aperture 1133 of the ball joint 1030 and this aperture 1133 is in communication to the larger aperture 1033 of the ball joint 1030 allowing the rotation of the final stage 1050 including the proximal cylindrical portion 1090 of the female element 1060 around the ball joint 1030 for at least 90°.

By acting manually on the enlarged annular ferrule 1080 of the distal portion 1055 it is possible to regulate the penetration of the threaded distal portion 1195 of the rod 1160 in the corresponding seat of the ball joint thus regulating the relative distance between the final stage 1050 and the first stage 1040. This also allows to reach the 90° "foldable" configuration of the connector 202 that is different from the working configuration wherein the angular movement between the first and the final stage 1040, 1050 is in the range 0° to 45°.

Figure 11B:
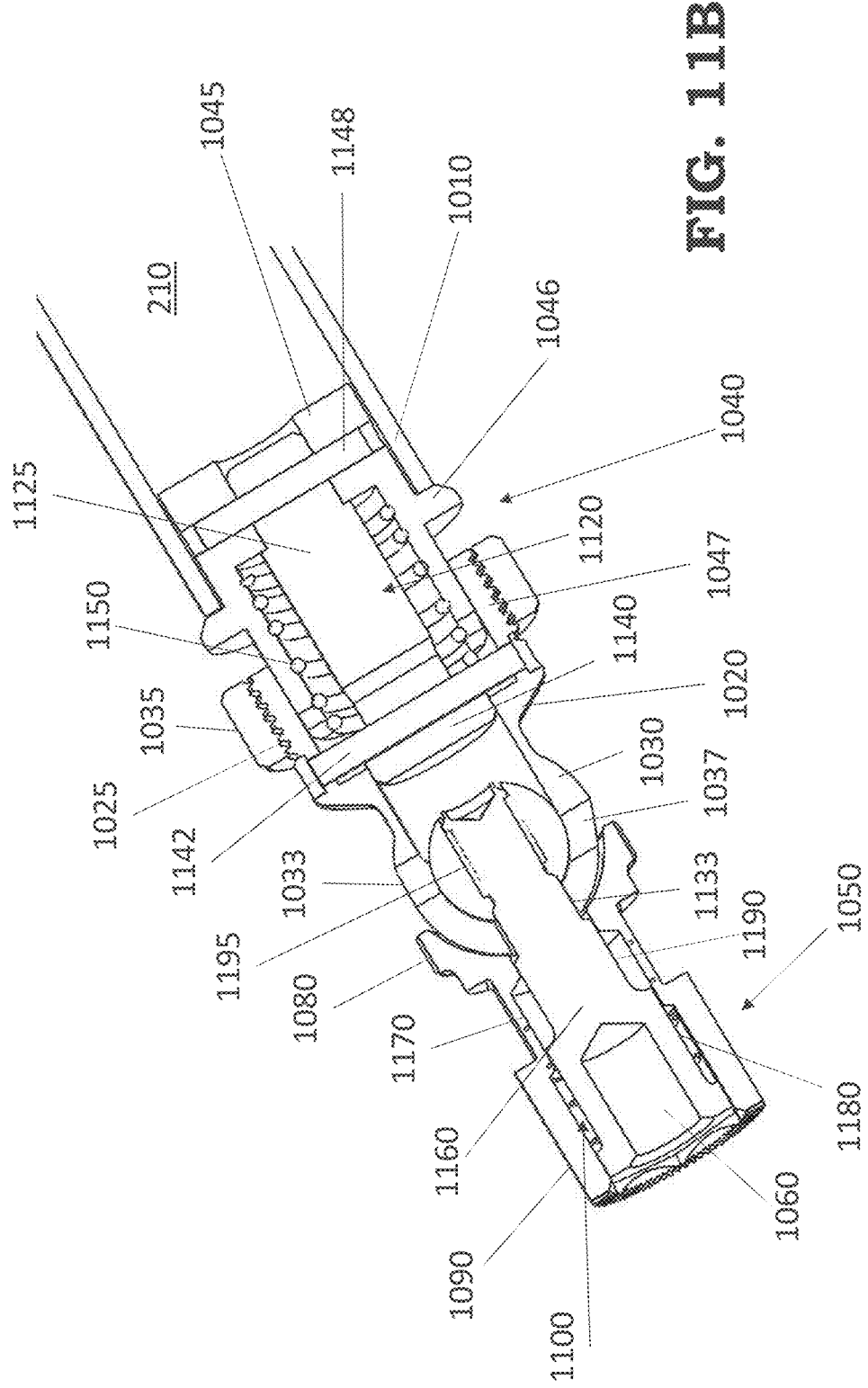
FIG. 11B is a further cross sectional view of the female connector of FIG. 11A taken from a perpendicular point of view.

FIG. 11B shows a cross sectional perspective view of the same female connector 202 of FIG. 11A but taken from a perpendicular point of view.

The components shown in this Figure are the same and report the same reference numbers of FIG. 11A.

In this figure it is particularly evident the T shaped inner shaft 1120 made in plastic material and assembled in the plastic support element 1045 together with the first transversal pin 1148 that is used to link the two plastic parts. The second transversal pin 1142 is also evident and is used as mechanical stop for the compression of the spring 1150 and to avoid any accidental disassembling of the strut.

The threaded adjustment ring 1035 is shown in a position closer to the base portion 1020 and wherein a gap is provided with respect to the end 1010 of the shaft 210 and with the spring 1150 released.

The larger aperture 1033 of the ball joint 1030 is also shown in comparison with the opposite one of the smaller apertures 1037.

FIG. 12A is another perspective view of the female connector of FIG. 10 taken from a different point of view.

FIG. 12B is a perspective view of the female connector of FIG. 10 wherein it is visible the internal spring-loaded mechanism 1100 including the spring 1111 wrapped around the rod 1160.

The rotation of the annular ferrule 1080 of the distal portion 1055 may regulate the compression of the spring 1111.

FIG. 12C is a slightly enlarged cross-sectional view of the female connector of FIG. 12B and, more specifically, of its final stage 1050 wherein it is clearly visible the distal threaded portion 1195 of the rod 1160 screwed in the seat provided in the ball joint 1030.

The rotation of the annular ferrule 1080 regulates the cohesion between the final stage 1050 and the first stage 1040 including the ball joint 1030 and allows rotating the final stage 1050 toward a greater angular movement for reaching the 90° "foldable" configuration.

Figures 13A, 13B, 13C:
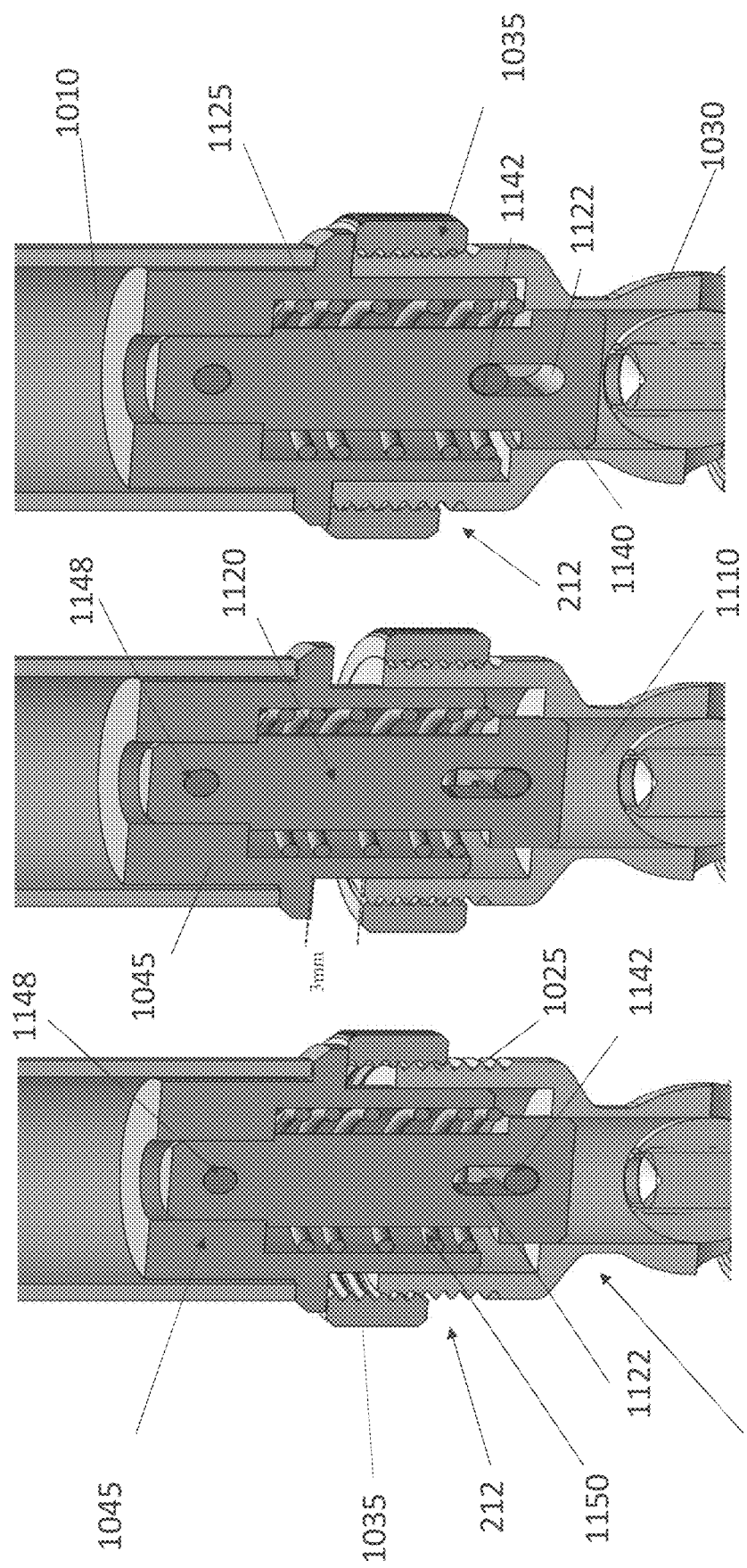
FIGS. 13A, 13B and 13C show enlarged cross-sectional views of the female connector of the present disclosure in different configurations, respectively.

FIG. 13A shows a cross-sectional view of the first stage 1040 of the female connection 202 and the adjustment mechanism 212 allowing an independent rapid and gradual fine adjustment in length of the strut 200.

As it may be appreciated, when the adjustment ring 1035 is abutting against the closing collar 1046 of the support element 1045 the screwing action of the adjustment ring may be exerted on the external threaded part 1025 of the base portion 1020 thus forcing the base portion 1020 to move toward the support element 1045.

The maximum extension of this screwing action may be regulated according to the needs. In a preferred embodiment disclosed herewith without limiting the Applicant's rights this maximum extension has been selected in 3 mm, as shown in FIG. 13B.

In the configuration of maximum extension of the FIGS. 13A and 13B the second transversal pin 1122 is located at one end of the elongated slot 1042 and the spring 1150 is its maximum relaxed extension.

FIG. 13C shows another cross-sectional view of the first stage 1040 wherein the adjustment ring 1035 is screwed on the largest portion of the external threaded part 1025 of the base portion 1020 while the enlarged portion 1140 of the T shaped inner shaft 1120 project more deeply toward the ball joint 1030 thus reducing the overall extension of the strut 200.

In this FIG. 13C it may be appreciated that in the final retracted configuration the second transversal pin 1122 is abutting against the opposite end of the elongated slot 1046, if compared with the other FIGS. 13A and 13B.

Figures 14A, 14B, 14C:
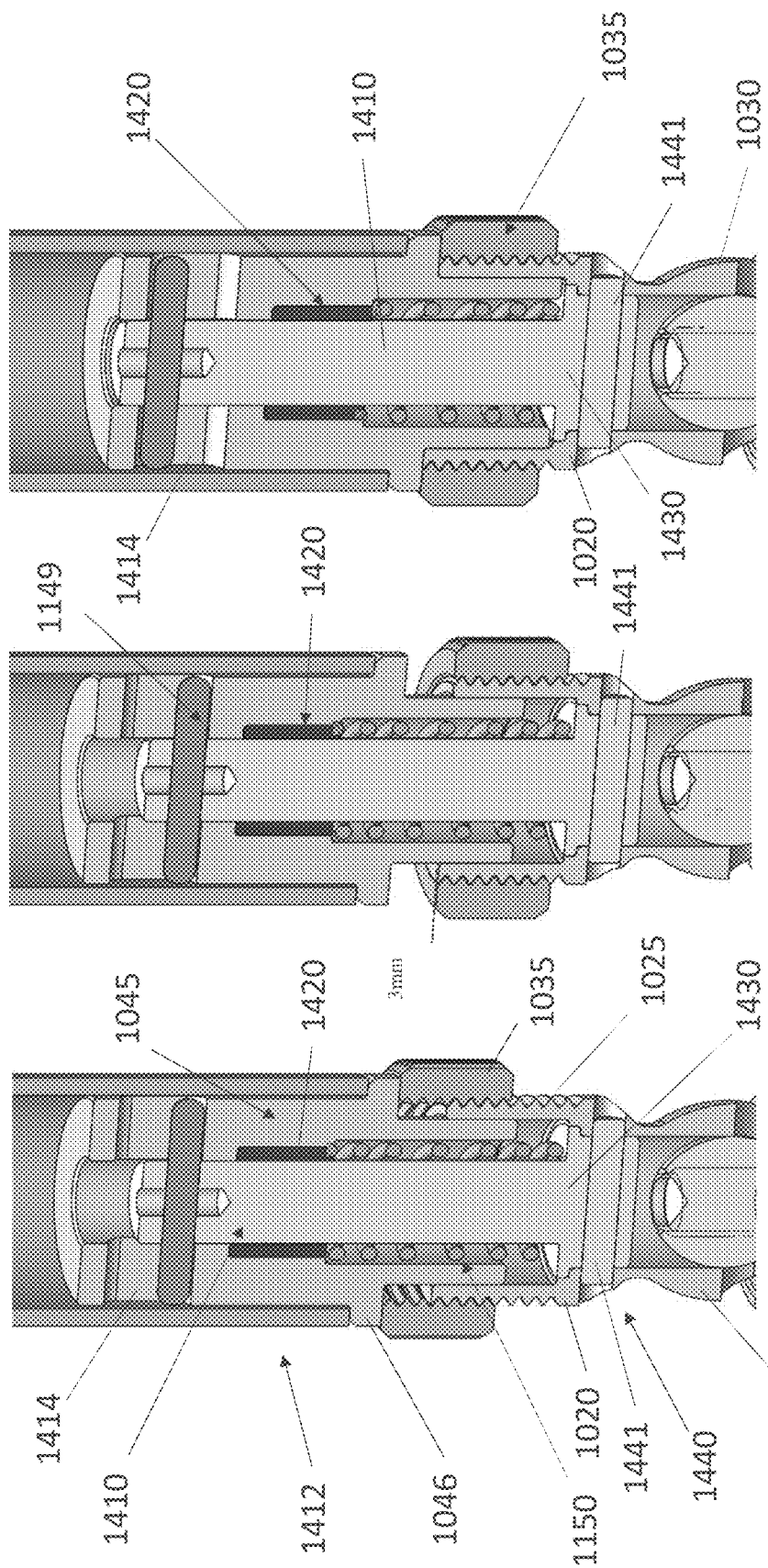
FIGS. 14A, 14B and 14C show enlarged cross-sectional views of an alternative embodiment of the female connector of the present disclosure in different configurations, respectively.

Now, with more specific reference to the FIGS. 14A to 14C it is disclosed an alternative embodiment of the female connector 202 of the present disclosure.

More specifically, the alternative embodiment relates to the dynamization adjustment mechanism 1412 associated to the female connector 202.

FIG. 14A is a cross-sectional view of an alternative embodiment of a dynamization mechanism 1412 associated to the first stage 1440 of the female connector 202 wherein parts and components having the same structure and functioning of the elements disclosed in previous FIGS. 10, 11, 12 and 13 are reported with the same reference numbers.

This alternative dynamization mechanism 1412 is provided with an inner shaft 1410 made by a radiolucent alloy, for instance Aluminum, fixed to the support element 1045 by a first distal transversal pin 1149.

A bushing 1420 is provided around the inner shaft 1410 at the bottom of the seat hosting the elastic element 1150. This bushing allows an easily movement between the two parts 1045 and 1410. In addition, a first distal transversal pin 1149 is fixed with the inner shaft 1410 and slides with this shaft inside a slot 1414 provided in the sleeve support element 1045. This transversal pin 1149 is used to avoid any accidental disassembling of the strut.

A terminal portion 1430 of the inner shaft 1410 is coupled in shape with an inner portion of the base portion 1020 and presents an enlarged portion crossed by a proximal second pin 1441 fixing this shaft to the base portion 1020. So, the dynamization mechanism 1412 associated to the first stage 1440 of this female connector embodiment provides for a fine adjustment in length for at least 3 mm in contrast with the compression of spring 1150 and with the distal transversal pin 1149 sliding inside the slot 1414.

Even in this embodiment when the adjustment ring 1035 is abutting against the closing collar 1046 of the support element 1045 the screwing action of the adjustment ring 1035 may be exerted on the external threaded part 1025 of the base portion 1020 thus forcing the base portion 1020 to move toward the support element 1045.

The maximum extension of this screwing action may be regulated according to the needs. In the preferred embodiment disclosed herewith without limiting the Applicant's rights this maximum extension has been selected in 3 mm, as shown in FIG. 14B.

FIG. 14C shows another cross-sectional view of the first stage 1440 wherein the adjustment ring 1035 is screwed on the largest portion of the external threaded part 1025 of the base portion 1020 while the first distal transversal pin 1149 has reached the an end of the slot 1414 compacting the base portion 1020 and the support element 1045 thus reducing the overall extension of the strut 200.

Now, with more specific reference to the FIGS. 15A to 15C it is disclosed an alternative embodiment of the female connector 202 of the present disclosure. More specifically, the alternative embodiment relates to the dynamization adjustment mechanism 1512 associated to the female connector 202.

FIG. 15A is a cross-sectional view of an alternative embodiment of a dynamization mechanism 1512 associated to the first stage 1540 of the female connector 202 wherein parts and components having the same structure and functioning of the elements disclosed in previous FIGS. 10, 11, 12 and 13 are reported with the same reference numbers.

As in previous embodiments, the radiolucent shaft end 1010 is closed by a support element 1545 formed as a double sleeve with a main portion inserted into the shaft end 1010, a collar 1546 abutting against the shaft end and a projecting portion 1547 supporting in a slidable manner the inner part of the base portion 1520 of the first stage 1540.

This alternative dynamization mechanism 1512 is provided with an inner shaft 1510 made by a radiolucent alloy, for instance Aluminum.

This inner shaft 1510 has one end 1530 provided with a threaded portion fixed to the base portion 1020 of the first stage 1540.

On the opposite distal end 1570 of the inner shaft 1510 there is a slot 1542 that is axially aligned along the longitudinal extension of the shaft 1510.

The main portion of the support element 1545 has a transversal pin 1548 passing through a slot 1542 provided in the inner shaft in the proximity of its distal end. The transversal pin 1548 is guided along the slot 1542 during the dynamization adjustment.

A collar 1560 is formed at a predetermined distance from the inner shaft end 1570 to support the elastic element, i.e. a spring 1550, that is trapped between such a collar 1560 and the transversal pin 1548.

As may be appreciated by the example of FIG. 15C, when the base portion 1520 of the first stage 1540 is completely retracted against the collar 1546 of the support element 1545 the pin 1548 is located at one end of the slot 1542 and the spring 1550 is compressed.

The dynamization mechanism of the FIGS. 15A, 15B and 15C is provided with an inner shaft made in Aluminum that is fixed though the first stage 1560 to the final female stage of the strut. The elastic element is housed in the distal main portion of the plastic support sleeve 1545 thus allowing to get a stronger plastic sleeve due to an increased material in the critical area more solicited. This construction and configuration help keeping in axis the parts, avoiding any accidental bending that could appear.

In addition, the transversal pin 1548 is used as mechanical stop for the compression of the spring 1550 to avoid any accidental disassembling of the strut.

The embodiments previously disclosed in their different structure have the common great advantage to provide a strut easy to use for the surgeon and very practical to transport in a sterilized package.

The use of reinforced plastic material for the connectors and the telescopic shafts 210 and 220 allows to reduce the overall strut weight and the outcome is a structure lighter if compared to the other similar devices of the prior art.

It will be understood that particular embodiments described herein are shown by way of illustration and not as limitations of the disclosure. The principal features of this disclosure can be employed in various embodiments without departing from the scope of the disclosure. Those skilled in the art will recognize, or be able to ascertain using no more than routine experimentation, numerous equivalents to the specific procedures described herein. Such equivalents are considered to be within the scope of this disclosure and are covered by the claims.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims

What is claimed is:

1. An improved external fixation strut comprising:
   an elongated body comprising a first and a second hollow tubular shaft;
   opposite connectors respectively coupled to an end portion of the first or the second shaft and each including a ball and socket joint;
   one shaft having an internal diameter that is slightly larger than an external diameter of the other shaft to host internally the other shaft in a slidably and telescopic manner;
   said first and second shafts of the strut being realized by a synthetic radiolucent plastic material;
   a clamp element provided in proximity of overlapping ends of the first and second shafts for providing a fast gripping action stopping the telescopic sliding of one shaft inside the other shaft;
   a manually operated fixation element acting on the clamp element for exerting said fast gripping action;
   a sleeve provided around a central portion of the strut where the first and second shafts overlap;
   the clamp element being a clamp band around said sleeve and including opposite and facing gripping portions, said gripping portions being connected by a threaded connector of the fixation element.

2. The improved external fixation strut of claim 1, wherein said fixation element has a head coupled to a removably manual butterfly wrench.

3. The improved external fixation strut of claim 1, wherein said sleeve is structured with a first sleeve portion having an internal diameter corresponding substantially to an external diameter of the first shaft and a second sleeve portion having an internal diameter corresponding substantially to an external diameter of the second shaft; said clamp band being around said second sleeve portion.

4. The improved external fixation strut of claim 1, wherein each ball and socket joint connector is structured to allow an angular movement of the corresponding connector with a spherical angle up to at least 90°.

5. The improved external fixation strut of claim 1, wherein a dynamization mechanism is associated to one of said opposite connectors and includes a first stage associated to one end of a shaft and comprising the ball and socket joint supported by a base portion, a screwed mechanism regulating projection of the base portion against an internal elastic element and a final stage including a female connector.

6. The improved external fixation strut of claim 5, wherein said base portion is axially and slidably coupled to a support element fixed to the shaft end and has an external treaded portion engaged by an adjustment ring abutting against the support element against elastic action of said internal elastic element.

7. The improved external fixation strut of claim 6, comprising an inner shaft fixed at one end to the support element and having a longitudinal slot at the other end, a transversal pin fixed to the base portion and slidable in said longitudinal slot and the elastic element wrapped around the inner shaft between its fixed end and the transversal pin.

8. The improved external fixation strut of claim 7, wherein the elastic element comprises a spring.

9. The improved external fixation strut of claim 5, wherein said dynamization mechanism includes radiolucent components.

10. The improved external fixation strut of claim 5, wherein said final stage is mechanically coupled to the ball joint of the first stage by a rod having one end screwed into the ball and socket joint and an opposite end provided with a female element of the female connector.

11. The improved external fixation strut of claim 10, wherein said rod is slidable inside the final stage against elastic action of a spring-loaded mechanism incorporated in the final stage around the rod.

12. The improved external fixation strut of claim 1, wherein a dynamization mechanism for an independent rapid and gradual fine dynamization adjustment in length of the strut is associated to a female connector and includes radiolucent components.

13. A fixation system including at least a first and a second fixation ring and/or at least a fixation arch interconnected by some fixation struts wherein at least one of said fixation struts comprises:
    an elongated body comprising a first and a second hollow tubular shaft;
    opposite connectors respectively coupled to an end portion of the first or the second shafts and each including a ball and socket joint;
    one shaft having an internal diameter that is slightly larger than an external diameter than the other shaft to host internally the other shaft in a slidably and telescopic manner;
    said first and second shafts of the strut being realized by a synthetic radiolucent plastic material;
    a clamp element provided in proximity of overlapping ends of the first and second shaft for providing a fast gripping action stopping the telescopic sliding of one shaft inside the other shaft;
    a manually operated fixation element acting on the clamp element for exerting said fast gripping action;
    wherein a dynamization mechanism including radiolucent components is associated to one of said opposite connectors and includes a first stage associated to one end of a shaft and comprising the ball and socket joint supported by a base portion, a screwed mechanism regulating projection of the base portion against an internal elastic element and a final stage including a female connector.

14. The fixation system of claim 13, wherein each strut comprises the opposite connectors each including a ball-and-socket joint allowing an angular movement of the corresponding strut with a spherical angle up to at least 90° for folding the fixation system for packaging and transportation purposes.

15. The fixation system of claim 13, wherein said base portion is axially and slidably coupled to a support element fixed to the shaft end and has an external treaded portion engaged by an adjustment ring abutting against the support element against elastic action of said internal elastic element.

16. The fixation system of claim 13, comprising:
    a sleeve provided around a central portion of the strut where the first and second shafts overlap;
    the clamp element being a clamp band around said sleeve and including opposite and facing gripping portions, at least one of the gripping portions having a central threaded hole receiving a threaded shaft of the fixation element.

17. An improved external fixation strut comprising:
    an elongated body comprising a first and a second hollow tubular shaft sliding in a telescopic manner one inside the other;
    a male connector coupled to an end portion of the elongated body and a female connector coupled to the opposite end portion of the elongated body;
    a ball and socket joint associated to each connector and configured for rotating according to a spherical angle up to at least 90°;
    a clamp element provided in proximity of overlapping ends of the first and second shafts for providing a fast gripping action stopping the telescopic sliding of one shaft inside the other shaft;
    a manually operated fixation element acting on the clamp element for exerting said fast gripping action;
    wherein a dynamization mechanism is associated to the female connector and includes a first stage associated to one end of a shaft and a final stage including the ball and socket joint supported by a base portion, a screwed mechanism is provided between the first and the final stages to regulate projection of the base portion against the action of an internal elastic element.

18. The improved external fixation strut of claim 17 wherein said first and second shafts of the strut are realized by a synthetic radiolucent plastic material.

19. The improved external fixation strut of claim 17 comprising:
    a sleeve provided around a central portion of the strut where the first and second shafts overlap;
    the clamp element being a clamp band around said sleeve and including opposite and facing gripping portions, at least one of the gripping portions having a central threaded hole receiving a threaded shaft of the fixation element.

20. The improved external fixation strut of claim 19, wherein said fixation element has a head coupled to a removably manual butterfly wrench.

21. The improved external fixation strut of claim 19, wherein one shaft has an internal diameter that is slightly larger than an external diameter of the other shaft to host internally the other shaft in a slidably and telescopic manner and said sleeve is structured with a first sleeve portion having an internal diameter corresponding substantially to an external diameter of the first shaft and a second sleeve portion having an internal diameter corresponding substantially to an external diameter of the second shaft; said clamp band being around said second sleeve portion.

22. The improved external fixation strut of claim 17, wherein said base portion is axially and slidably coupled to a support element fixed to the shaft end and has an external treaded portion engaged by an adjustment ring abutting against the support element against elastic action of said internal elastic element.

23. The improved external fixation strut of claim 22, comprising an inner shaft fixed at one end to the support element and having a longitudinal slot at the other end, a transversal pin fixed to the base portion and slidable in said longitudinal slot and the elastic element wrapped around the inner shaft between its fixed end and the transversal pin.

24. The improved external fixation strut of claim 23, wherein the elastic element comprises a spring.

25. The improved external fixation strut of claim 17, wherein said dynamization mechanism includes radiolucent components.

26. The improved external fixation strut of claim 17, wherein the dynamization mechanism is configured for an independent rapid and gradual fine dynamization adjustment in length of the strut and includes radiolucent components.

* * * * *